(12) United States Patent
Jimbo et al.

(10) Patent No.: US 6,635,879 B2
(45) Date of Patent: Oct. 21, 2003

(54) APPARATUS FOR AND METHOD OF DETECTING RADIATION SOURCE

(75) Inventors: Masao Jimbo, Otawara (JP); Takeshi Sasaki, Isesaki (JP); Shuji Tsuchiya, Fujisawa (JP); Kenzo Eguchi, Machida (JP); Hao Wei, Ichikawa (JP); Katsuroh Ohwadano, Tokyo (JP); Hideki Ryuo, Fujisawa (JP)

(73) Assignee: Anzai Medical Kabushiki Kaisha, Tokyo (JP)

( * ) Notice: Subject to any disclaimer, the term of this patent is extended or adjusted under 35 U.S.C. 154(b) by 135 days.

(21) Appl. No.: 09/892,580

(22) Filed: Jun. 28, 2001

(65) Prior Publication Data

US 2002/0117627 A1 Aug. 29, 2002

(30) Foreign Application Priority Data

Feb. 28, 2001 (JP) ........................................ 2001-055742

(51) Int. Cl.[7] ................................................ G01T 1/20
(52) U.S. Cl. .............................. 250/370.13; 250/370.01
(58) Field of Search ...................... 250/370.13, 370.01, 250/370.09, 370.11, 370.12, 332, 338.4, 363.04, 252.1, 336.1; 600/436

(56) References Cited

U.S. PATENT DOCUMENTS

| 5,248,885 A | * | 9/1993 | Sato et al. ............. 250/370.15 |
| 5,857,463 A | * | 1/1999 | Thurston et al. ............ 600/436 |
| 5,907,329 A | * | 5/1999 | Nobutani et al. ............ 345/537 |
| 6,101,038 A | * | 8/2000 | Hebert et al. ................ 359/618 |
| 6,172,362 B1 | * | 1/2001 | Lingren et al. .......... 250/252.1 |
| 6,399,951 B1 | * | 6/2002 | Paulus et al. .......... 250/370.13 |
| 6,472,668 B1 | * | 10/2002 | Griesmer et al. ...... 250/370.13 |
| 2002/0021292 A1 | * | 2/2002 | Sakashita .................... 345/204 |

* cited by examiner

*Primary Examiner*—Constantine Hannaher
*Assistant Examiner*—Otilia Gabor
(74) *Attorney, Agent, or Firm*—Paul A. Guss

(57) ABSTRACT

A small-size gamma camera is capable of reliably and quickly detecting the accumulated position of a radiation source in an examinee. When the examinee is scanned with the gamma camera which has an area sensor comprising 256 (16×16) semiconductor detecting elements, display elements of a display unit on a rear panel of the gamma camera are turned on to display a pattern indicative of the accumulated position of the radiation source. According to the displayed pattern on the display elements, the operator of the gamma camera moves the gamma camera to detect the accumulated position of the radiation source reliably within a short period of time.

16 Claims, 18 Drawing Sheets

ASSOCIATION TABLE OF DISPLAYED LUMINANCE LEVELS OR HEADPHONE SOUND LEVELS

APPARATUS FOR AND METHOD OF DETECTING RADIATION SOURCE

BACKGROUND OF THE INVENTION

1. Field of the Invention

The present invention relates to an apparatus for and a method of detecting the accumulated position of a radioisotope (hereinafter referred to as "RI"), i.e., the position of a radiation source, administered or injected into an examinee, and displaying the detected position on a light-emitting element assembly or a display device.

2. Description of the Related Art

For detecting the position of an RI administered or injected into an examinee, it has heretofore been customary for the operator to scan the examinee with a gamma probe (small-size gamma-ray detector), which comprises a scintillator and a PMT (photomultiplier tube) and has a detecting surface having a diameter ranging from 5 to 10 mm, held by hand, and determine the position where the detected electric output signal or detected sound is of a maximum level as the accumulated position of the RI.

The conventional process relies upon the operator's senses to look for the position where the detected electric output signal or detected sound, which is converted from the detected electric output signal, is of a maximum level. Therefore, the process is disadvantageous in that the examinee often needs to be scanned on a trial-and-error basis, and, because the detecting surface is small as its diameter ranges from 5 to 10 mm, it takes the operator a considerable period of time until the accumulated position of the RI, i.e., the position of the radiation source, is detected.

In addition, since the gamma probe has only one radiation-to-electric conversion element or pixel, the process is unable to identify the accumulated position of the RI accurately even when it is detected.

The gamma probe with only one radiation-to-electric conversion element fails to meet a demand for the observation of an accumulated distribution of the RI on the examinee.

The PMT of the gamma probe is required to be operated under a high voltage and hence needs a large drive circuit. While the gamma probe itself may be of a relatively small size, the power supply device including the drive circuit for energizing the probe is large in size, and cannot easily be handled in use.

SUMMARY OF THE INVENTION

It is therefore an object of the present invention to provide a radiation source detecting apparatus which is of a simple arrangement capable of displaying an accumulated distribution of an RI.

Another object of the present invention is to provide a radiation source detecting apparatus which is capable of detecting the accumulated position of an RI reliably within a short period of time, and which can easily be handled in use.

Still another object of the present invention is to provide a radiation source detecting apparatus which is capable of rendering a distributed image of an RI on a display device or the like.

Yet another object of the present invention is to provide a radiation source detecting method which is capable of detecting the accumulated position of an RI reliably within a short period of time.

According to the present invention, a radiation emitted from a radiation source in an examinee is detected by an area sensor having a plurality of detecting elements, a distribution of the radiation source is detected by a signal processor based on signals outputted from the detecting elements, and the determined distribution of the radiation source is displayed by an image display unit. Therefore, the operator can recognize the distribution of the radiation source in the examinee from the displayed image.

According to the present invention, furthermore, when an examinee having a radiation source for emitting a radiation is scanned by an area sensor having a plurality of detecting elements, a position/direction display unit displays a pattern indicative of a position/direction of the radiation source which is determined by a signal processor based on signals outputted from the detecting elements. By operating the area sensor according to the displayed pattern, the operator can recognize the position of the radiation source, i.e., the accumulated position of a radioisotope in the examinee, reliably within a short period of time.

The display unit may display the determined distribution and/or position/direction of the radiation source. The operator can recognize the accumulated position of the radioisotope in the examinee reliably within a short period of time, and can also recognize the distribution of the radiation source in the examinee at the same time.

According to the present invention, furthermore, when an examinee is scanned with an area sensor disposed in a portion of a main unit having a prismatic shape and having a plurality of detecting elements, a display unit disposed in another portion of the main unit displays the determined distribution and/or position/direction of the radiation source which is determined by a signal processor based on signals outputted from the detecting elements. By operating the area sensor according to the displayed distribution and/or position/direction of the radiation source, the operator can recognize the position of the radiation source, i.e., the accumulated position of a radioisotope in the examinee, reliably within a short period of time, and also recognize the distribution of the radiation source in the examinee at the same time.

The display unit may comprise a single display unit including a display area for displaying the distribution of the radiation source and a display area for displaying the position/direction of the radiation source. Accordingly, the display unit can be produced inexpensively.

The display areas may be disposed in different positions or suitable members may be used as the respective display areas. For example, light-emitting diodes may be used as the display area for displaying the position/direction of the radiation source, and a liquid crystal display unit may be used as the display area for displaying the distribution of the radiation source. The liquid crystal display unit can easily display the intensity of the distribution, and the light-emitting diodes can clearly indicate the position/direction of the radiation source. If the position/direction display unit comprises a plurality of display areas for displaying the position/direction of the radiation source, then the operator can easily know the position/direction of the radiation source from a display on a certain one of the display areas.

If the display areas comprise arrow indicators disposed in a radial pattern, then the operator can easily know the position/direction of the radiation source from the orientation of one of the arrow indicators which is turned on.

The signal processor may comprise means for controlling flickering intervals of the display areas depending on the determined position/direction of the radiation source, or means for controlling displayed luminance levels of the display areas depending on the determined position/direction of the radiation source. These means allow the operator to visually recognize quickly whether the area sensor is approaching the position of the radiation source or not.

According to the present invention, there is also provided an apparatus for detecting a radiation source, comprising an area sensor having a plurality of detecting elements for detecting a radiation emitted from a radiation source in an examinee, a signal processor for processing signals outputted from the detecting elements into an audio signal, and audio output means for outputting sound and/or voice sound based on the audio signal from the signal processor, the signal processor comprising means for controlling the audio output means to generate sound and/or voice sound indicative of a position/direction of the radiation source.

With the above arrangement, since the position/direction of the radiation source is indicated by sound and/or voice sound, the operator can recognize the radiation source through the auditory sense.

The sound indicative of the position/direction of the radiation source may comprise a sound having a predetermined intensity and/or a predetermined frequency.

The voice sound indicative of the position/direction of the radiation source may comprise a voice sound representing the direction of a time on an analog clock whose center is regarded as the center of the area sensor.

Each of the detecting elements may comprise a CdTe or a CdZnTe semiconductor detecting element.

According to the present invention, there is further provided an apparatus for detecting a radiation source, comprising an area sensor having a plurality of radiation detecting elements, as many memories as the number of the radiation detecting elements, for storing respective output signals from the radiation detecting elements, and a signal processor for reading the output signals of the radiation detecting elements from the memory and processing the read output signals, the signal processor comprising means for combining a predetermined number of output signals or all output signals from the radiation detecting elements and outputting an image and/or audio signal based on the combined output signals.

Since the radiation detected in a small area can be displayed in a wide area or outputted as an audio signal, the operator can easily recognize the radiation source.

The detecting elements should preferably comprise n×m (n, m represent at least 2) detecting elements.

According to the present invention, there is also provided a method of detecting the position of a radiation source with an area sensor having a plurality of radiation detecting elements which provide a radiation detecting surface, comprising the steps of combining a predetermined number of output signals from the radiation detecting elements to cause the area sensor to function as a reduced number of radiation detecting elements without changing the area of the radiation detecting surface, combining a progressively reduced number of output signals from the radiation detecting elements to cause the area sensor to function as a progressively increased number of radiation detecting elements without changing the area of the radiation detecting surface, and finally, causing the area sensor to function as the plurality of radiation detecting elements.

Even if the radiation source is detected in a small area in the radiation detecting area of the area sensor, since the small area is one of the divided areas of the radiation detecting area of the area sensor, it is easy for the operator to specify the position of the radiation source.

All output signals from the radiation detecting elements may be combined to cause the area sensor to function as a single radiation detecting element without changing the area of the radiation detecting surface. This process allows the operator to recognize the presence of the radiation source quickly.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
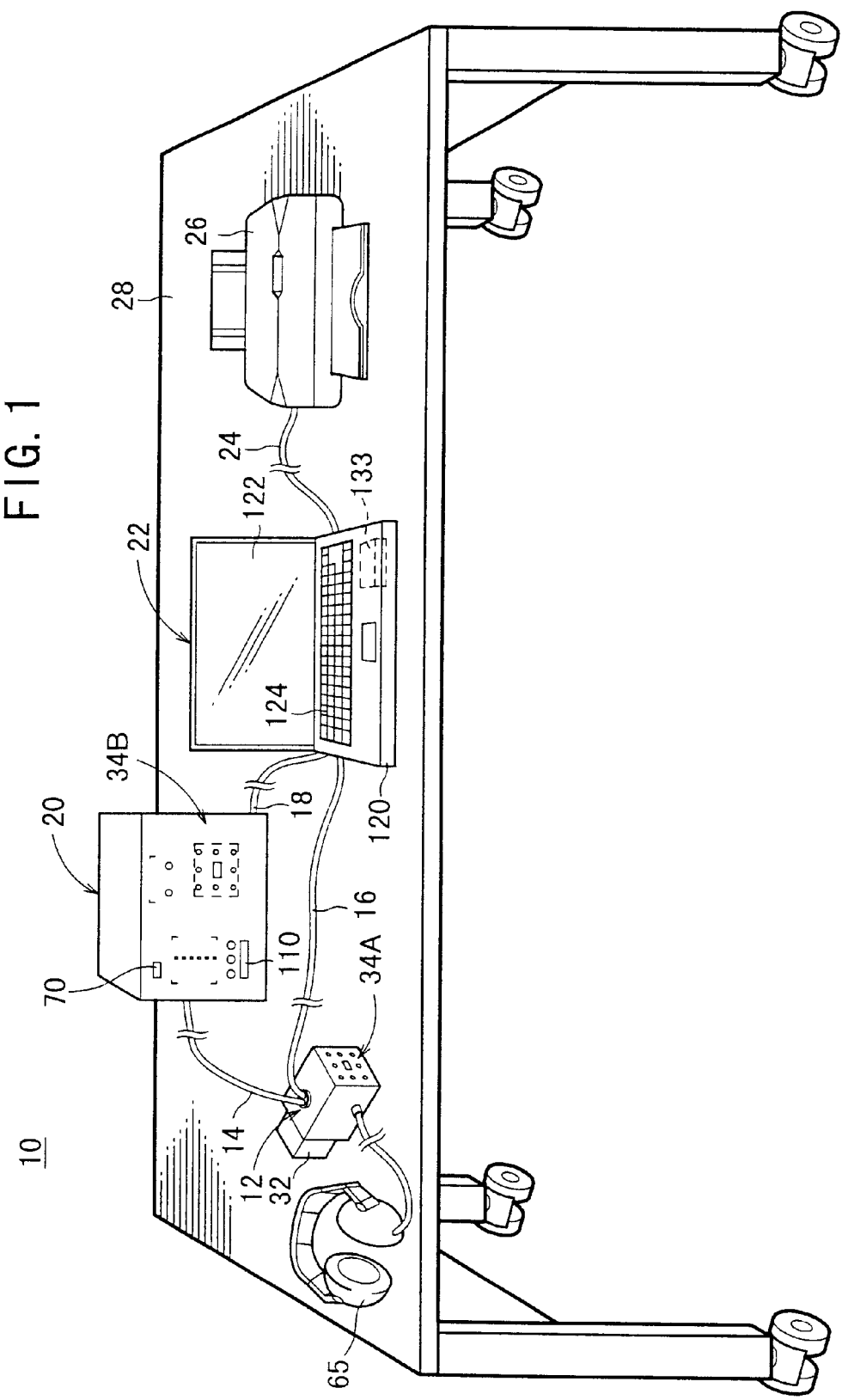
FIG. 1 is a perspective view of a radiation source detecting system according to an embodiment of the present invention.

FIG. 1 shows in perspective a radiation source detecting system 10 according to an embodiment of the present invention.

As shown in FIG. 1, the radiation source detecting system 10 basically comprises a gamma camera 12 as a manually operable radiation source detecting apparatus, a control box 20 connected to the gamma camera 12 by a communication cable 14, and a personal computer 22 connected to the gamma camera 12 by a communication cable 16. The personal computer 22 and the control box 20 are also connected to each other by a communication cable 18. A printer 26 is connected to the personal computer 22 by a communication cable 24.

The communication cables 14, 16, 18 have connection terminals on their both ends, and the gamma camera 12, the control box 20, and the personal computer 22 have connectors for connection to the connection terminals of the communication cables 14, 16, 18. The function of the communication cable 16 may be performed by the communication cables 14, 18. If the function of the communication cable 16 is performed by the communication cables 14, 18, then the communication cable 16 may be dispensed with.

The radiation source detecting system 10 is disposed on a movable table 28, which allows the radiation source detecting system 10 to move to a position near an examinee (not shown) lying on an examination bed (not shown).

Figure 2:
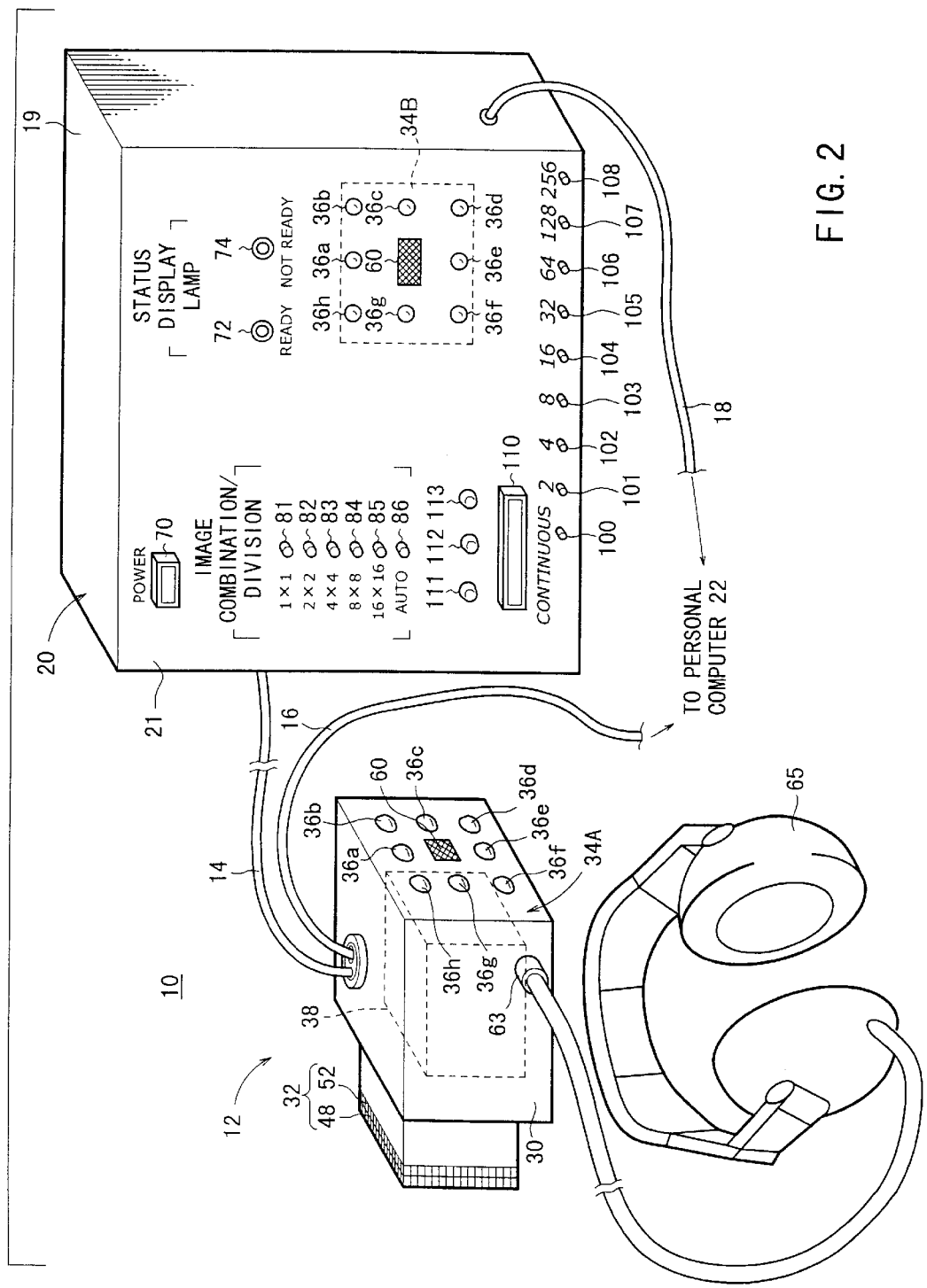
FIG. 2 is a perspective view of a gamma camera and a control box of the radiation source detecting system shown in FIG. 1.

FIG. 2 shows in perspective the gamma camera 12 and the control box 20 in greater detail.

The gamma camera 12 comprises a main unit 30 in a prismatic shape surrounded by a casing, an area sensor 32 mounted on a front face of the main unit 30, which becomes a lower face when it scans the examinee lying on the examination bed, and a position/direction display unit 34A mounted on a rear face of the main unit 30, which becomes an upper face when it scans the examinee lying on the examination bed. The gamma camera 12 has an overall volume of about 6 cm (front face)×6 cm (rear face)×20 cm (height).

Figure 3:
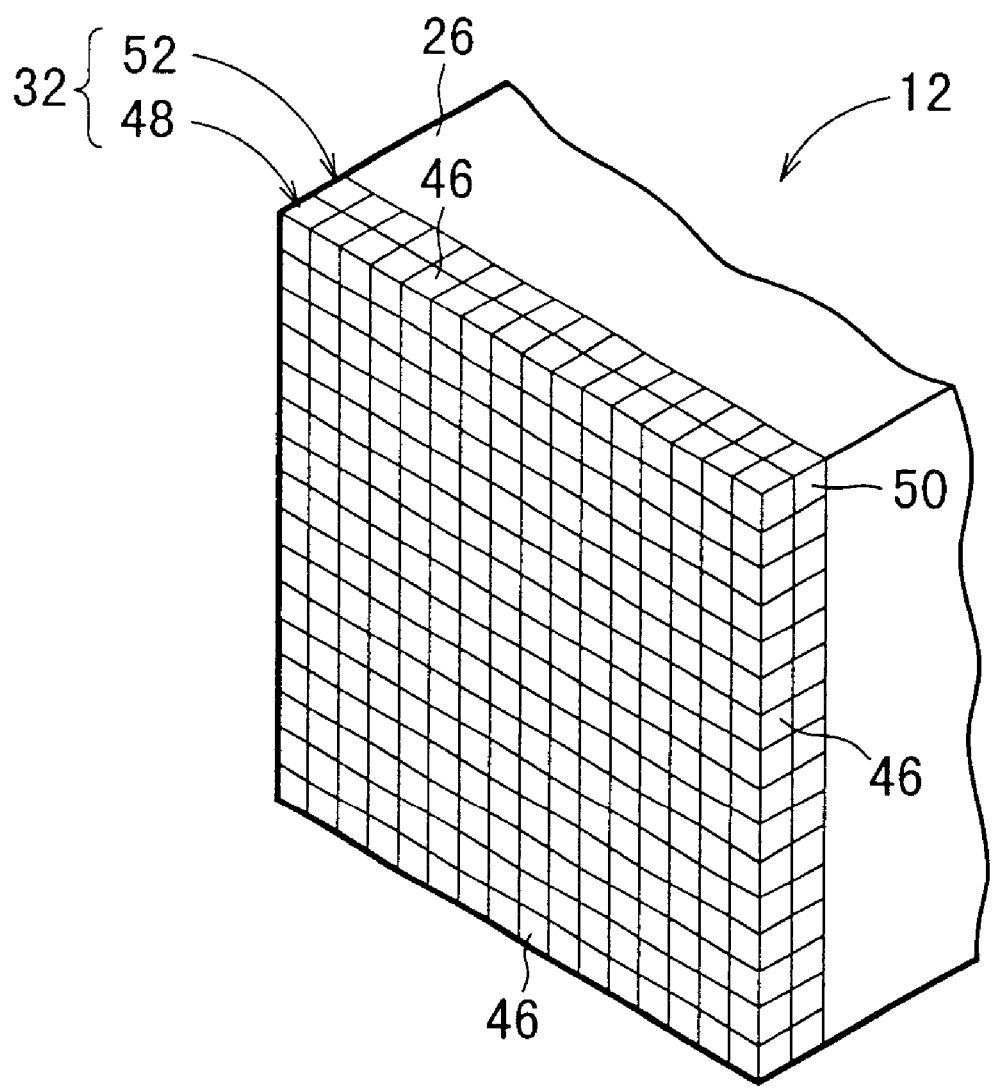
FIG. 3 is a perspective view of an area sensor mounted on a tip end of the gamma camera.

As also shown in FIG. 3, the area sensor 32 comprises a two-dimensional image sensor (area sensor) having a collimator array 48 of 256 (16×16) collimators 46 for facing the examinee, the collimator array 48 providing a surface for detecting a radiation emitted from a radioisotope (RI), and a detecting element array 52 of 256 (16×16) detecting elements 50 associated respectively with the collimators 46. The detecting elements 50 may comprise CdTe semiconductor detecting elements or CdZnTe semiconductor detecting elements. In the present embodiment, the detecting elements 50 serve as radiation-to-electric conversion elements or pixels for detecting radiation particles radiated from a radiation source in the examinee and converting the detected radiation particles into an electric signal.

In the area sensor 32, only the collimator array 48 is movable in the axial direction of the gamma camera 12 relatively to the detecting element array 52 while being kept parallel to the detecting element array 52.

As shown in FIG. 2, the control box 20 also has a position/direction display unit 34B, which is identical to the position/direction display unit 34A, disposed on a control panel 21. Each of the position/direction display units 34A, 34B comprises eight display elements 36a through 36h in the form of LEDs (light-emitting diodes) for emitting amber light.

The display elements 36a through 36h include four display elements 36b, 36d, 36f, 36h that are positioned respectively on the vertexes of a square and four display elements 36a, 36c, 36e, 36g that are positioned respectively on midpoints of sides of the square, as the position/direction display units 34A, 34B are viewed in front elevation.

The gamma camera 12 is of such a shape and structure that when the operator carries the gamma camera 12 by hand, the display element 36a points to 12:00 on an analog clock, i.e., in the upward direction, and can move the gamma camera 12 over the examinee lying on the examination bed.

When the area sensor 32 faces the examinee lying on the examination bed, therefore, the display elements 36a through 36h of the position/direction display unit 34A are present in the directions of 12:00 (upper), 01:30 (upper right), 03:00 (right), 04:30 (lower right), 06:00 (lower), 07:30 (lower left), 09:00 (left), and 10:30 (upper left). The display elements 36a through 36h may be arranged in a circular pattern for better analogy to an analog clock.

In the gamma camera 12, the position/direction display unit 34A and the area sensor 32 are electrically connected to a signal processor 38 that is accommodated in the main unit 30. The area sensor 32 detects a radiation emitted from a radiation source, i.e., a radioisotope RI, in the examinee, and the signal processor 38 determines the position/direction of the radiation source based on a signal outputted from the area sensor 32, and displays the information about the determined position/direction on the position/direction display unit 34A.

The signal processor 38 supplies a signal representing the determined position/direction information via the communication lines 14, 16 to the position/direction display unit 34B of the control box 20 and the personal computer 22. When the signal processor 38 determines the position/direction of the radiation source, the signal processor 38 determines an intensity distribution of the radiation from the radiation source based on signals outputted from all the 256 semiconductor detecting elements 50. The intensity distribution of the radiation from the radiation source detected by the semiconductor detecting elements 50 can be displayed as an image, as described later on.

The position/direction information produced by the signal processor 38 can be outputted as sound or voice from loudspeakers 60 that are disposed centrally on the position/direction display units 34A, 34B. The loudspeakers 60 can be switched on and off by the personal computer 22 or the control box 20. The gamma camera 12 may have a button switch for switching on and off the loudspeakers 60.

The main unit 30 of the gamma camera 12 has on a side panel thereof a connection terminal 63 for connection to headphones 65. When the headphones 65 are connected to the connection terminal 63, the connection is detected by the signal processor 38, which sends information representing the connection to the control box 20. At this time, the sound or voice indicative of the position/direction information produced by the signal processor 38 is not outputted from the loudspeakers 60, but from the headphones 65.

The control box 20 has a main unit 19 connected to an AC power supply of AC 100 V or the like by a power supply plug (not shown). The control panel 21 of the control box 20 has a power supply switch 70 comprising an illumination type push-button switch which is illuminated when turned on.

The control box 20 also functions as a power supply of the gamma camera 12 in the present embodiment. When the power supply switch 70 is turned on, the control box 20 supplies electric energy to the gamma camera 12 via the communication cable 14 that comprises a multicore cable. When the control box 20 supplies electric energy to the gamma camera 12, a power supply lamp on the gamma camera 12 is turned on.

The control panel 21 has status indicator lamps 72, 74 comprising a measurement ready lamp (READY) and a measurement not ready lamp (NOT READY), respectively, which are positioned on the right-hand side of the power supply switch 70. The instant the power supply switch 70 is turned on, the measurement not-ready lamp 74 is turned on to emit red light. When a measurement mode is ready, the measurement not-ready lamp 74 is turned off and the measurement ready lamp 72 is turned on to emit green light.

The control panel 21 also has five pixel combination/division switches comprising illumination-type ganged push-button switches. These switches include a 1×1 pixel switch 81, a 2×2 pixel switch 82, a 4×4 pixel switch 83, an 8×8 pixel switch 84, a 16×16 pixel switch 85, and an automatic pixel number setting (AUTO) switch 86. These pixel combination/division switches are used to establish display settings on the position/direction display units 34A, 34B, as described later on.

The control panel 21 also has nine radiation capture time determining switches 100 through 108 which comprise illumination-type ganged push-button switches. The radiation capture time determining switch 100 is a switch for commanding continuous radiation capture. The other radiation capture time determining switches 101 through 108 are switches for specifying radiation capture times of 2, 4, 8, 16, 32, 64, 128, and 256 seconds, respectively. The radiation capture time determining switches 100 through 108 may comprise slide switches, rather than push-button switches.

The control panel 21 further has an image capture switch 110 comprising a push-button switch and three lamps 111, 112, 113 comprising light-emitting diodes for indicating a present capture status depending on the number of times that the image capture switch 110 has been pressed. When the lamps 111, 112, 113 are turned on, they emit green light, yellow light, and red light, respectively.

If the image capture switch 110 is pressed once while the measurement ready lamp 72 is being turned on, then a process of measuring and collecting radiation data begins. While the radiation from the examinee is being captured, the time set by one of the radiation capture time determining switches 100 through 108 is measured by a timer (not shown). The green lamp 111 is flickered during the time being measured by the timer, and then de-energized upon elapse of the time.

If the image capture switch 110 is pressed again while the green lamp 111 is being flickered, then the process of measuring and collecting radiation data is temporarily stopped and the timer operation is also interrupted, and the green lamp 111 is turned off and the yellow lamp 112 is flickered. If the image capture switch 110 is pressed once more, then the process of measuring and collecting radiation data is resumed and the timer operation is also resumed, and the green lamp 111 is flickered and the yellow lamp 112 is turned off. If the image capture switch 110 is pressed once again, then the green lamp 111 is turned off and the red lamp 113 is flickered. After the red lamp 113 is flickered for a given period of time, the process of measuring and collecting radiation data is finished.

If the image capture switch 110 is pressed continuously for a relatively long time, e.g., 3 seconds or more in the present embodiment, while the process of measuring and collecting radiation data is being carried out with the green lamp 111 being initially flickered or while the process of measuring and collecting radiation data is being temporarily stopped with the yellow lamp 112 being flickered, then the process of measuring and collecting radiation data is interrupted, and the radiation data that has been collected so far is reset.

As shown in FIG. 1, the personal computer 22 comprises a main unit 120 having a central processing unit (CPU), a hard disk 133 as a memory, etc., a display unit 122 connected to the main unit 120, and an input unit 124 connected to the main unit 120 and comprising a keyboard or a pad. The printer 26 which is connected to the personal computer 22 by the communication cable 24 serves as an image output device.

Figure 4:
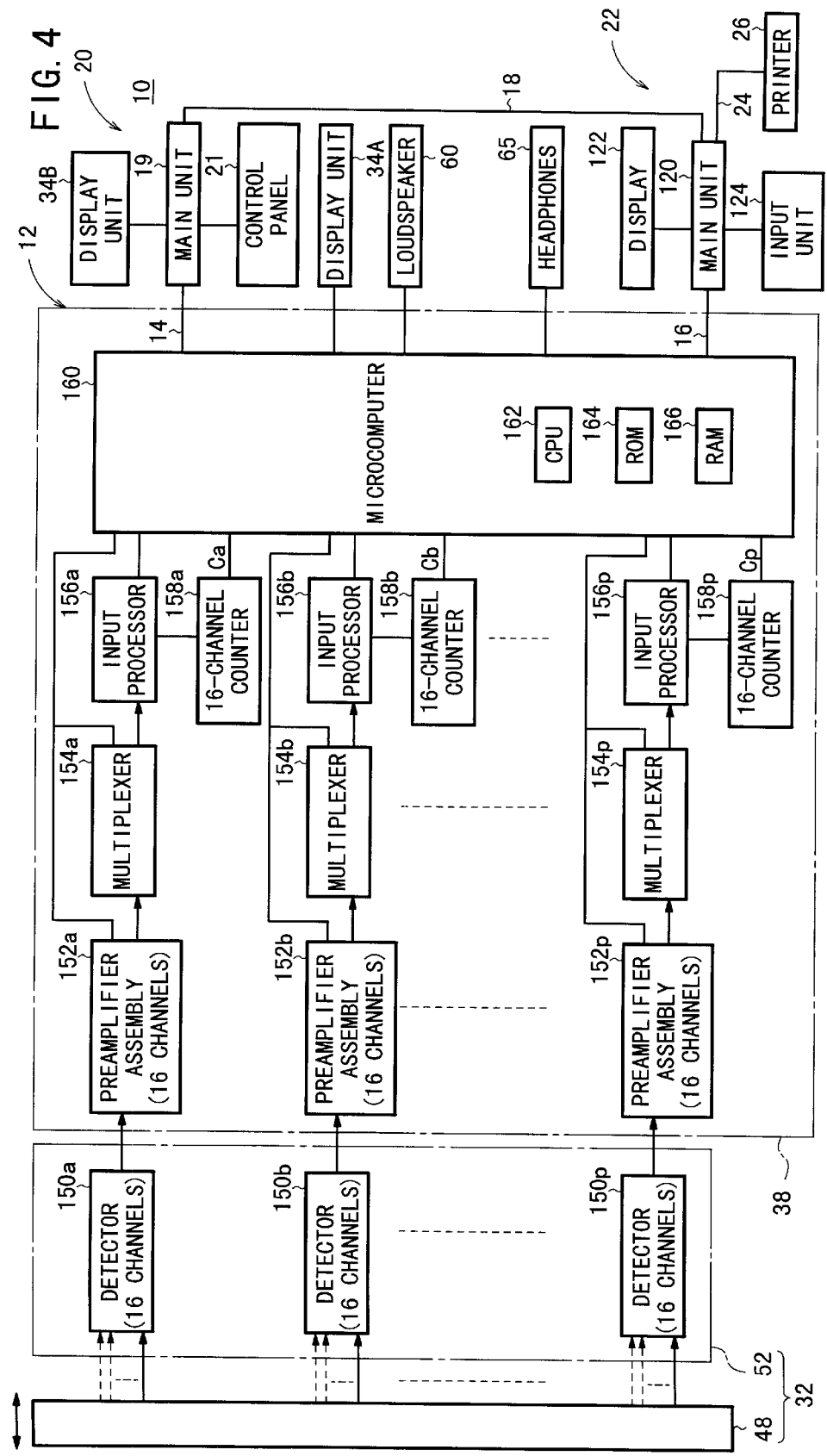
FIG. 4 is a block diagram of an electric circuit of the radiation source detecting system shown in FIG. 1.

FIG. 4 shows in block form an electric circuit of the radiation source detecting system 10 shown in FIG. 1.

Figure 5:
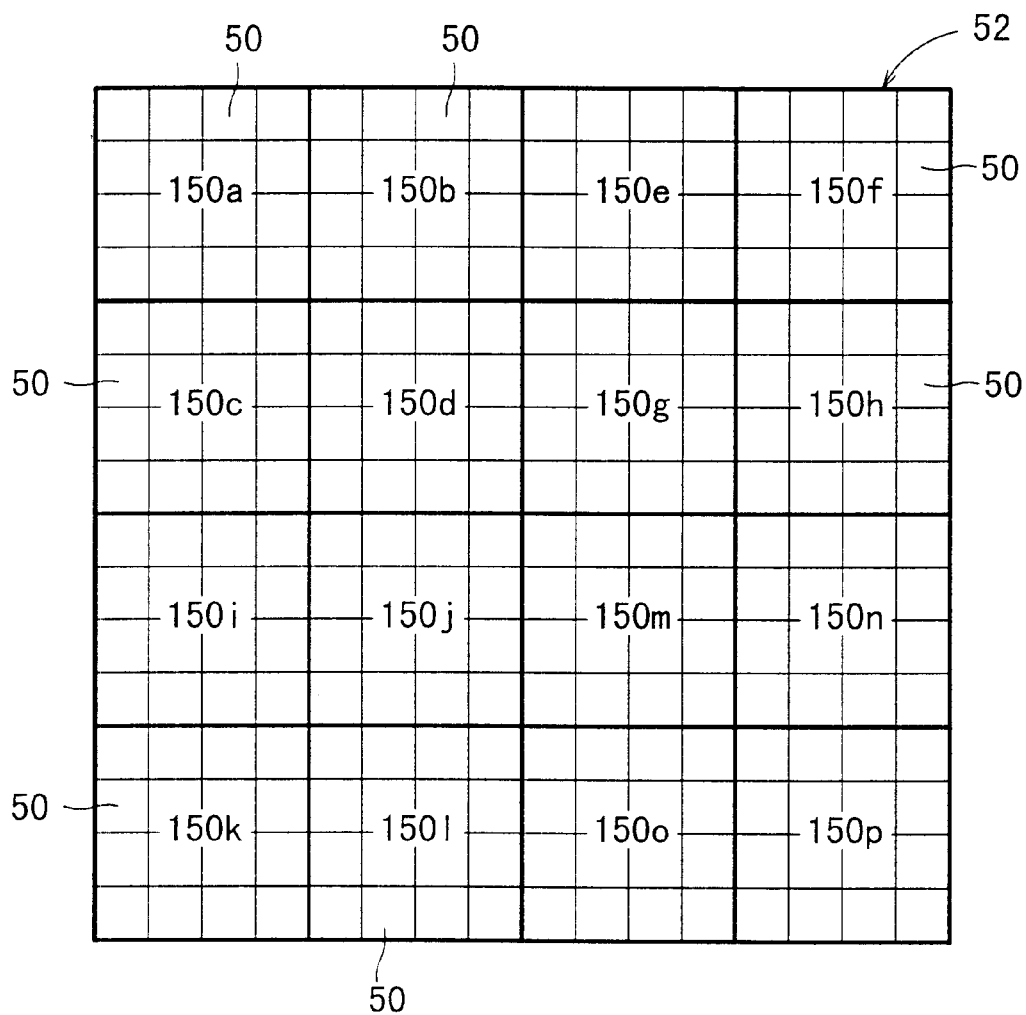
FIG. 5 is a front elevational view of a detecting element array of the area sensor.

FIG. 5 shows in front elevation the detecting element array 52 of the area sensor 32. The detecting element array 52 is of a square shape having a size of 32 mm×32 mm.

As shown in FIGS. 4 and 5, the detecting element array 52 of the area sensor 32 has 16 detectors 150 (150a through 150p) for detecting the radiation emitted from the radiation source in the examinee through the collimator array 48.

Each of the detectors 150 comprises 16 (4×4) semiconductor detecting elements 50 each having a size of about 2 mm×2 mm. Each of the detectors 150 has a size of about 8 mm×8 mm.

Because the area sensor 32 has a size determined by the above size of the detectors 150, the gamma camera 12 with the 16 detectors 150 for detecting the radiation emitted from the radiation source in the examinee, i.e., gamma rays in the present embodiment, can easily be operated by hand, i.e., can easily be manually operated.

The 16 detectors 150a through 150p, each composed of 16 semiconductor detecting elements 50, also referred to as 16 channels, output pulse signals representing the radiation. These pulse signals are supplied to preamplifier assemblies 152 (152a through 152p), each comprising 16 preamplifiers or channels, of the signal processor 38.

Each of the preamplifiers of the preamplifier assemblies 152 has a function to amplify the pulse signal outputted from one of the semiconductor detecting elements 50, and removes noise from the pulse signal. The amplification factor and the noise removal range, i.e., frequency and level window settings, can be set for each of the preamplifiers by a microcomputer 160 based on instructions entered from the input unit 124 of the personal computer 22.

The pulse signals amplified by the preamplifier assemblies 152 are multiplexed by 16:1 multiplexers 154 (154a through 154p), and supplied to input processors 156 (156a through 156p).

Each of the multiplexers 154 is switched at a high speed not to produce a readout error (loss) of pulse signals under the control of the microcomputer 160. Each of the multiplexers 154 is capable of substantially simultaneously reading pulse signals in all the 16 channels even though it successively reads one at a time of 16 pulse signals.

Each of the input processors 156 converts the pulse signals in the respective channels into binary pulse signals using a window having given levels, i.e., a low level and a high level. The input processors 156 supply the pulse signals to respective 16-channel counters (counting circuits, counting means, counting units) 158 (158a through 158p). The counters 158 count the supplied pulse signals in the respective channels either continuously if the radiation capture time determining switch 100 is pressed or during a preset period of time which may be one of the radiation capture times of 2, 4, 8, 16, 32, 64, 128, and 256 seconds specified by the radiation capture time determining switches 101 through 108. The counters 158 hold their counts in the 16×16 channels, i.e., 256 counts for the respective semiconductor detecting elements 50. The counters 158 are reset to zero each time the preset period of time expires.

When the counters 158 are reset, their counts are transferred from the counters 158 to a RAM 166 in the microcomputer 160 where the counts are held. The data of the intensity distribution of the radiation from the radiation source which are held in the RAM 166 are supplied to and stored in the hard disk 133 in the main unit 120 of the personal computer 22 via the communication cable 16. The gamma camera 12 may have a programmable ROM such as a flash memory or the like for storing the data of the intensity distribution of the radiation from the radiation source.

The microcomputer 160 comprises a central processing unit (CPU) 162, a read-only memory (ROM) 164 for storing a signal processing program and an operating system (OS), a RAM 166 for temporarily storing data, and input/output interfaces (not shown). These components of the microcomputer 160 are interconnected by a bus (not shown).

The counts C {Ca (Ca1 through Ca16) through Cp (Cp1 through Cp16)} of the counters 158 are stored in respective given addresses in the RAM 166. As described above, the counts C are also stored in the hard disk 133 in the main unit 120 of the personal computer 22.

Figure 6:
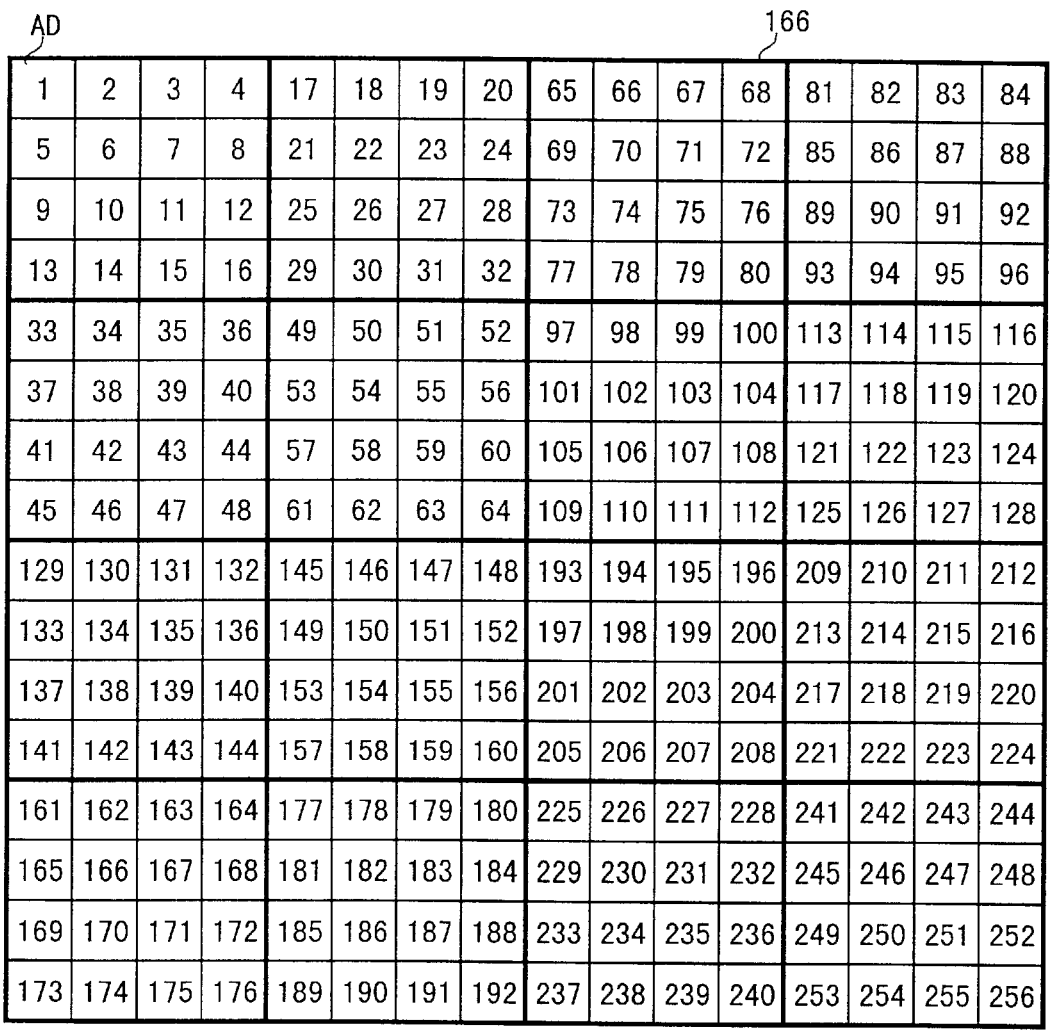
FIG. 6 is a diagram showing an address layout of a memory for holding the output signals from detecting elements as counts.

FIG. 6 shows a memory map of the RAM 166 by way of example. As shown in FIG. 6, the RAM 166 has 256 addresses AD1 through AD256 each capable of storing N-bit data (14-bit data in the present embodiment) D1 through D256. The data D1 through D256 stored in the respective addresses AD1 through AD256 represent the numbers of gamma rays detected by the respective semiconductor detecting elements 50, i.e., the counts C {Ca (Ca1 through Ca16) through Cp (Cp1 through Cp16)}, counted continuously or in the preset period of time. For example, the address AD1 stores the count C=Ca1, and the address AD256 stores the count C=Cp16.

Based on the signal processing program, the microcomputer 160 controls the multiplexers 154, the input processor 156, and the 16-channel counters 158, processes the counts C of the 16-channel counters 158, stores an image signal based on the processed counts C in the RAM 166, and transmits the image signal to the main unit 19 of the control box 20 and the personal computer 22 via the communication cables 14, 16. The control box 20 also has its microcomputer housed in the main unit 19.

The processing operation of the microcomputer 160 of the gamma camera 12 can be performed by the control box 20 or the personal computer 22. The control box 20 and the gamma camera 12 may be integrally combined with each other. If the control box 20 and the gamma camera 12 are integrally combined with each other, then the power supply of the gamma camera 12 should preferably be constructed as a separate power supply adapter in order to reduce the size and weight of the integral assembly.

The position/direction display unit 34A and the loudspeakers 60 are connected to the microcomputer 160. The headphones 65 are connected to the microcomputer 160 as required by the operator.

The personal computer 22 stores image signals captured by the gamma camera 12 into its hard disk 133.

The main unit 120 of the personal computer 22 displays an image based on image information represented by the intensity distribution of the radiation, which has been supplied directly from the gamma camera 12 or supplied via the control box 20 from the gamma camera 12, or an image generated by the main unit 120 itself, on the display unit 122.

The radiation source detecting system 10 according to the present embodiment is basically constructed and operates as described above.

Signal processing operation of the microcomputer 160 which is controlled by the personal computer 22 as a host computer, particularly with respect to data display on the position/direction display units 34A, 34B, will be described below with reference to FIG. 7.

As described above, the processing sequence of the microcomputer 160 can be performed by the control box 20 or the personal computer 22.

Figure 7:
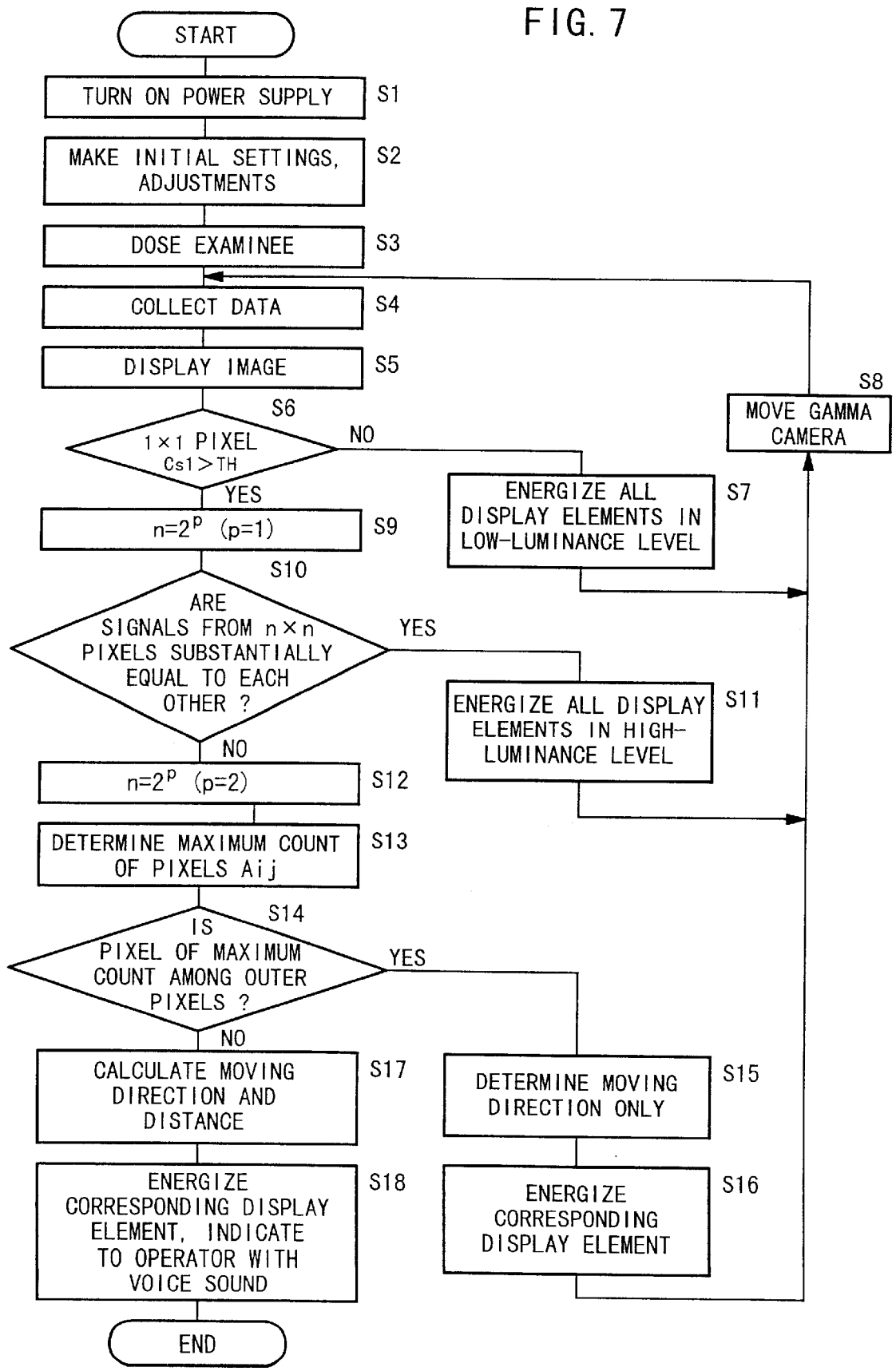
FIG. 7 is a flowchart of an operation sequence of the radiation source detecting system shown in FIG. 1.

In step S1 shown in FIG. 7, the personal computer 22 is turned on, and the power supply switch 70 of the control box 20 is pressed to turn on the control box 20. When the control box 20 is turned on, the measurement not-ready lamp 74 is energized to indicate that the measurement mode is not ready, and the control box 20 supplies DC electric energy to the gamma camera 12.

When the DC electric energy is supplied to the gamma camera 12, the gamma camera 12 diagnoses itself. If the diagnosis of the gamma camera 12 indicates no malfunction, then the gamma camera 12 sends the diagnosed result to the control box 20. In response to the diagnosed result, the control box 20 turns off the measurement not-ready lamp 74 and turns on the measurement ready lamp 72.

In step S2, a calibrating standard gamma ray is applied to the detectors 150a through 150p, and the amplification factor and noise removal range of each of the preamplifier assemblies 152 are set and the window levels of the input processors 156 are determined in order to enable the 16-channel counters 158 to produce predetermined counts C.

The operator of the gamma camera 12 then determines a data capture time. It is assumed that the operator presses the switch 102 to set the data capture time to 4 seconds. Of the pixel combination/division switches used to establish display settings on the position/direction display units 34A, 34B, the operator presses the automatic pixel number setting switch 86 to automatically set a pixel number.

Initialization of the gamma camera 12 is now completed.

In step S3, the examinee to be scanned by the gamma camera 12 is dosed with a labeling solution of a radioisotope of technetium ($^{99m}$Tc), e.g., tin colloid. The injected technetium ($^{99m}$Tc) is accumulated in an afflicted local region in the examinee, e.g., a cancer tissue or a blood flow disturbance (thrombus) in peripheral vein. Therefore, the afflicted local region serves as a radiation source, and emits a radiation or a gamma ray as a pulse signal. Movement of a radioisotope within a lymph duct can also be observed.

Thereafter, a manual processing operation to detect the afflicted local region is started. In step S4, the operator places the headphones 65 against its ears, carries the gamma camera 12 by hand, holds the area sensor 32 as a radiation detecting surface against the examinee, and presses the image capture switch 110 once in order to begin detecting the radiation (gamma ray). Now, the gamma camera 12 detects the radiation from the examinee for 4 seconds that have been set by the switch 102. That is, data of the radiation emitted from the examinee is collected for 4 seconds.

More specifically, the radiation emitted from the examinee, which comprises gamma-ray particles, is detected by the area sensor 32 having the collimator array 48 and detecting element array 52, and converted to electric pulse signals by the 256 (16×16) semiconductor detecting elements 50 of the detecting element array 52.

The electric pulse signals from the respective semiconductor detecting elements 50 are supplied via the preamplifier assemblies 152, the multiplexers 154, and the input processors 156 to the 16-channel counters 158. The 16-channel counters 158 count the electric pulse signals for 4 seconds, and supply respective counts C corresponding to the respective 256 semiconductor detecting elements 50 to the RAM 166, which stores the supplied counts C as data.

In step S5, an image representing a distribution of the radiation from the radiation source, which comprises 16×16 (256) pixels, is displayed as a black-and-white image on the display unit 122 of the personal computer 22 based on the 256 counts C. The resolution of each pixel is represented by a count $C=2^N=2^{14}=8192$. The counts C are converted to suitable gradations, which are displayed on the display unit 122.

In step S6, a pseudo 1 pixel detecting process, i.e., a pseudo (1×1) pixel detecting process, is carried out in order to identify the position/direction of the radiation source. The pseudo 1 pixel detecting process is a process of adding all the counts C from the 16-channel counters 158 (158a through 158p) into a sum count Cs1 to regard the 256 semiconductor detecting elements 50 as a single detecting element, i.e., to regard the 256 pixels as one large pixel, for detecting whether there is a radiation source or not.

The sum count Cs1 (Cs1=Ca1+Ca2+ . . . +Ca15+Ca16) is compared with a certain threshold TH, which is established to avoid the influence of noise, to determine whether there is a radiation source or not. The threshold TH may be set to a value which is twice the sum count Cs1 that is generated for a given period of time, i.e., 4 seconds set by the switch 102, at the time of no signal in the absence of the examinee, or to a value manually entered from the input unit 124 of the personal computer 22.

If the sum count Cs1 is smaller than the threshold TH in step S6, then the microcomputer 160 judges that there is no radioisotope signal from the examinee, and energizes all the display elements 36a through 36h of the position/direction display units 34A, 34B in a low-luminance level in step S7. Alternatively, the microcomputer 160 may energizes all the display elements 36a through 36h in a flicker mode.

Figure 8A:
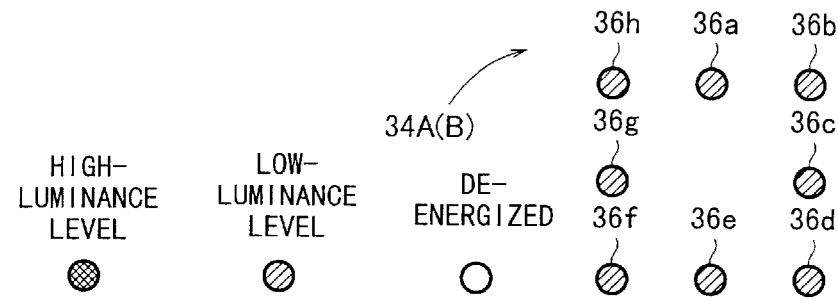
FIG. 8A is a view showing a display pattern on a display unit when a radiation source cannot be identified.

FIG. 8A shows a display pattern on the display elements 36a through 36h of the position/direction display units 34A, 34B when the microcomputer 160 judges that there is no radioisotope signal from the examinee. In FIGS. 8A through 8D, cross-hatched circular dots represent the display elements 36a through 36h which are energized in a high-luminance level, hatched circular dots represent the display elements 36a through 36h which are energized in a low-luminance level, and non-hatched, i.e., blank, circular dots represent the display elements 36a through 36h which are not energized. Alternatively, the display elements 36a through 36h may be energized such that they, as represented by the cross-hatched circular dots, are flickered at shorter intervals than those represented by the hatched circular dots.

Figure 9C:
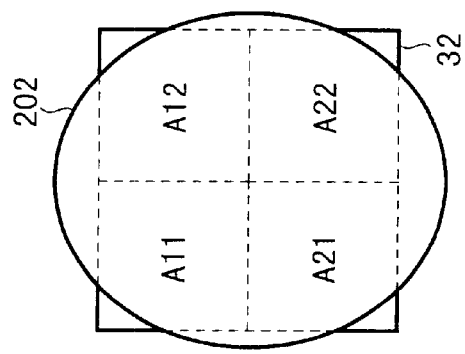
FIG. 9C is another view showing the relative positional relationship between the area sensor and the radiation source when the radiation source is positioned centrally on the area sensor.
Figure 9F:
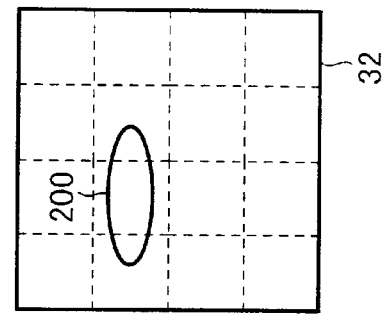
FIG. 9F is a view showing the relative positional relationship between the area sensor and the radiation source when the radiation source is positioned within the area sensor.
Figure 9B:
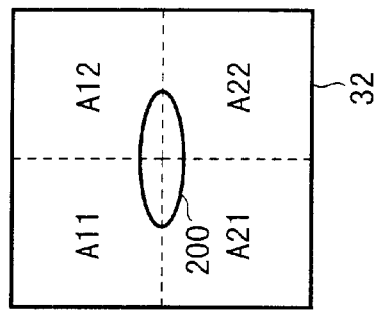
FIG. 9B is a view showing the relative positional relationship between the area sensor and the radiation source when the radiation source is positioned centrally on the area sensor.
Figure 9E:
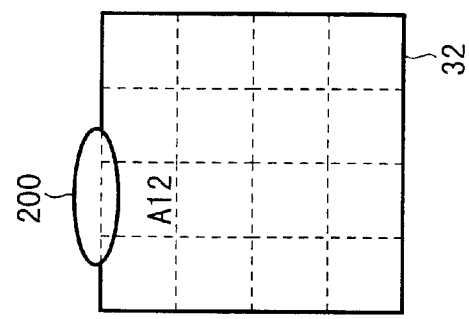
FIG. 9E is a view showing the relative positional relationship between the area sensor and the radiation source when the radiation source is positioned in the direction of 12:00 on the area sensor.
Figure 9A:
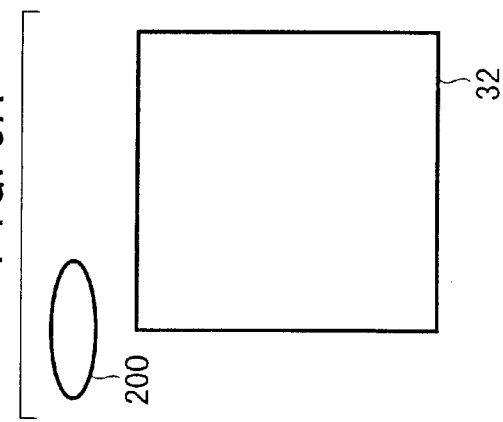
FIG. 9A is a view showing the relative positional relationship between the area sensor and the radiation source when the radiation source is spaced from the area sensor.

FIG. 9A shows in plan the relative positional relationship between the area sensor 32 as projected onto the examinee and a radiation source 200 in the examinee when the display pattern shown in FIG. 8A is displayed on the display elements 36a through 36h. FIG. 9A indicates that if the sum count Cs1 is smaller than the threshold TH in step S6, then the radiation source 200 and the area sensor 32 are spaced from each other.

Then, the operator who is manually handling the gamma camera 12 while looking at the display elements 36a through 36h which are energized in the low-luminance level, as shown in FIG. 8A, moves the gamma camera 12 to another location on the examinee by a distance corresponding to a diagonal line, for example, of the detecting surface of the area sensor 32 in step S8. Then, the operator presses the image capture switch 110 again for collecting radiation data in step S4. Thereafter, an image is displayed on the collected radiation data in step S5.

It is now assumed that the sum count Cs1 is greater than the threshold TH in step S6. Then, control goes to step S9.

In step S9, the number of pixels on one side of the square-shaped detecting element array 52 is represented by n and a parameter by p, and the number of pixels on one side of a pseudo pixel assembly is set to n=$2^P$ (p=1)=2 to perform a pseudo 2×2 pixel detecting process which involves a total of 2×2=4 pixels.

In step S10, the microcomputer 160 determines whether the counts C from the four pixels in the pseudo 2×2 pixel detecting process are substantially equal to each other or not. The 2×2=4 pixels involved in the pseudo 2×2 pixel detecting process include a pixel composed of the detectors 150a through 150d, a pixel composed of the detectors 150e through 150h, a pixel composed of the detectors 150i through 150l, and a pixel composed of the detectors 150m through 150p. These four pixels are represented as pixels Aij (i=1, 2, j=1, 2).

Specifically in step S10, the microcomputer 160 determines whether the sum counts Cs11=Ca1+Ca2+ . . . +Cd16, Cs12=Ce1+Ce2+ . . . +Ch16, Cs13=Ci1+Ci2+ . . . +Cl16, Cs14=Cm1+Cm2+ . . . +Cp16 of the pixels of the four pixels Aij (i=1, 2, j=1, 2) are substantially equal to each other or not.

If the sum counts are substantially equal to each other, then it is judged that the radiation source 200 or a radiation source 202 is present centrally on the area sensor 32 as shown in FIG. 9B or 9C.

Figure 8B:
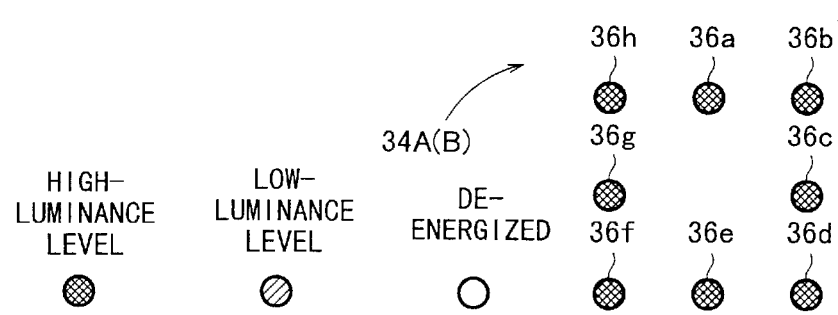
FIG. 8B is a view showing a display pattern on the display unit when a radiation source is detected centrally on the area sensor.

If the sum counts are substantially equal to each other in step S10, then all the display elements 36a through 36h of the position/direction display units 34A, 34B are energized in the high-luminance level, as shown in FIG. 8B, in step S11.

By looking at the displayed pattern shown in FIG. 8B, the operator understands that the center of the radiation source 200 or 202 is located immediately below the gamma camera 12, i.e., the area sensor 32.

Thereafter, control goes to the processing of step S8 for detecting another radiation source, if necessary. Usually, it is rare at an initial state of examination for the microcomputer 160 to find that the sum counts are substantially equal to each other in step S10.

If the sum counts are not substantially equal to each other in step S10, i.e., if a radiation source has been detected in the pseudo 1 pixel detecting process in step S6, but it is impossible to identify the direction of the radiation source with respect to the area sensor 32 in the 2×2 pixel detecting process in step S9, then the number of pixels on one side of the pseudo pixel assembly is set to n=$2^P$ (p=2)=4 to perform a pseudo 4×4 pixel detecting process which involves a total of 4×4=16 pixels in step S12.

In step S13, the microcomputer 160 determines a maximum count of pixels Aij (i=1 through 4, j=1 through 4) in the pseudo 4×4 pixel detecting process.

In step S14, the microcomputer 160 determines whether the pixel with the maximum count C is present among the outermost pixels (i.e., pixels A11 through A14, A21, A24, A31, A34, A41 through A44, see FIGS. 10A through 10D) or not. If the pixel with the maximum count C is present among the outermost pixels, then the microcomputer 160 determines only the direction of the pixel with respect to the area sensor 32, i.e., the direction in which to move the gamma camera 12, in step S15. Then, in step S16, one of the display elements 36a through 36h which corresponds to the determined direction is energized in the high-luminance level. Thereafter, the microcomputer 160 performs the processing in steps S8 through S14.

If the pixel with the maximum count C is not present among the outermost pixels in step S14, then since the pixel with the maximum count C is present among central four pixels (i.e., pixels A22, A23, A32, A33), the microcomputer 160 calculates the direction in which to move the gamma camera 12 and the distance by which to move the gamma camera 12 in step S17. Based on the calculated direction and distance, the microcomputer 160 turns on corresponding one of the display elements 36a through 36h, and outputs voice sound through the headphones 65 to indicate the calculated direction and distance to the operator in step S18.

Figure 9D:
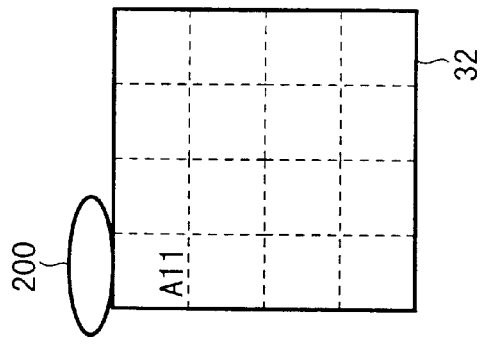
FIG. 9D is a view showing the relative positional relationship between the area sensor and the radiation source when the radiation source is positioned in the direction of 10:30 on the area sensor.

If the pixel with the maximum count C is present among the outermost pixels in step S14, the radiation source 200 is positioned at the pixel A11 of the area sensor 32 shown in FIG. 9D or at the pixel A21 of the area sensor 32 shown in FIG. 9E.

Figure 8C:
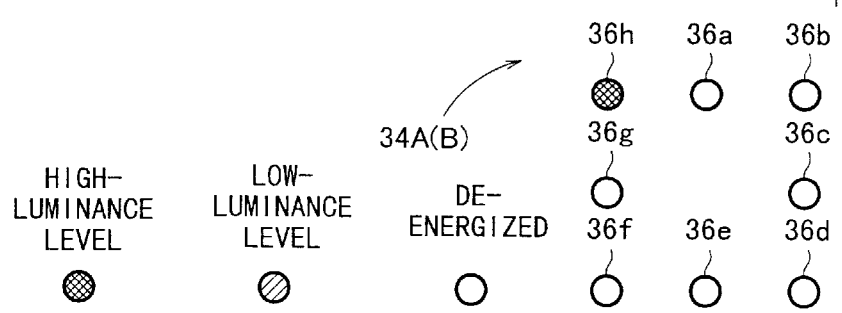
FIG. 8C is a view showing a display pattern on the display unit when a radiation source is detected in the direction of 10:30 on the area sensor.
Figure 8D:
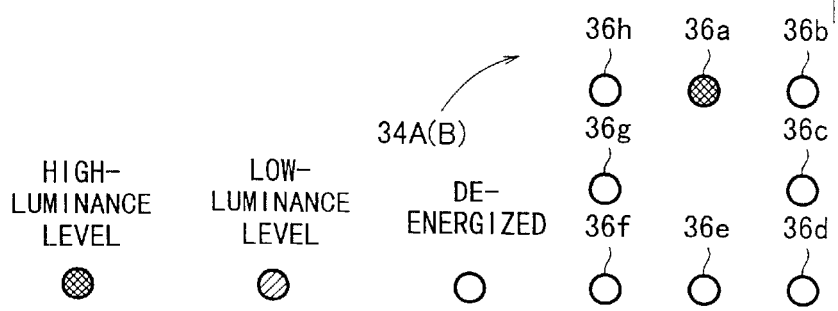
FIG. 8D is a view showing a display pattern on the display unit when a radiation source is detected in the direction of 12:00 on the area sensor.

At this time, based on the image shown in FIG. 9D, only the display element 36h in the direction of 10:30 is displayed in the high-luminance level in the position/direction display units 34A, 34B, as shown in FIG. 8C. Therefore, the operator can move the gamma camera 21 in the direction of 10:30 in step S8. Alternatively, based on the image shown in FIG. 9E, only the display element 36a in the direction of 12:00 is displayed in the high-luminance level in the position/direction display units 34A, 34B, as shown in FIG. 8D. Therefore, the operator can move the gamma camera 21 in the direction of 12:00 in step S8.

If the pixel with the maximum count C is not present among the outermost pixels in step S14, the radiation source 200 is positioned within the area sensor 32, e.g., at a position shown in FIG. 9F. In this case, the operator can observe the image shown in FIG. 9F on the display unit 122 of the personal computer 22. In FIG. 9E, the image on the area sensor 32 can also be observed on the display unit 122 of the personal computer 22.

FIGS. 10A through 10D show display patterns on the display elements 36a through 36h when the radiation source 200 is positioned within the area sensor 32 at the time the area sensor 32 operates in the pseudo 4×4 pixel detecting process.

Figure 10A:
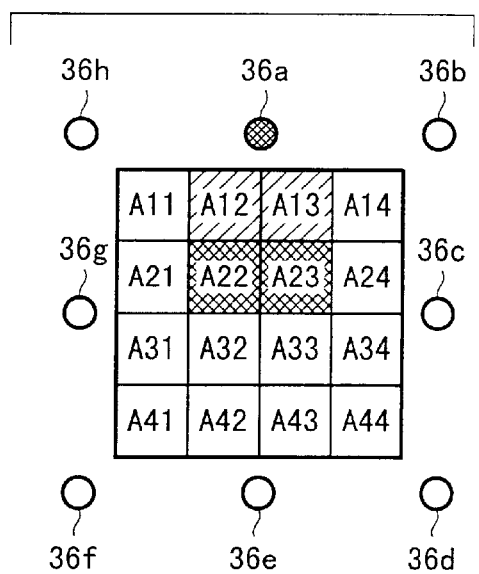
FIG. 10A is a view showing a display pattern on the display unit when display elements in the direction of 12:00 are turned on in a pseudo 4×4 pixel detecting process that is carried out when the radiation source is positioned within the area sensor.
Figure 10B:
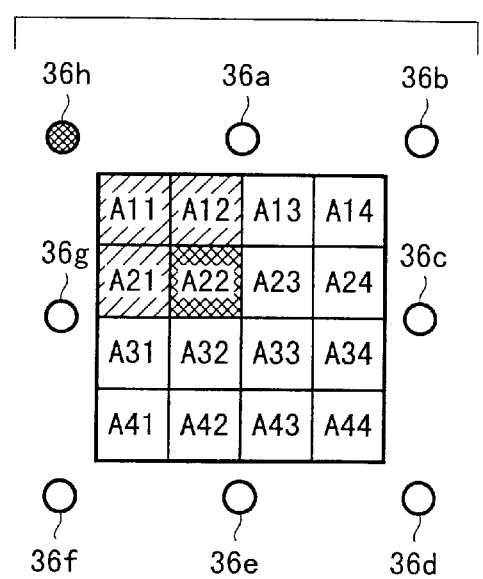
FIG. 10B is a view showing a display pattern on the display unit when display elements in the direction of 10:30 are turned on in the pseudo 4×4 pixel detecting process that is carried out when the radiation source is positioned within the area sensor.
Figure 10C:
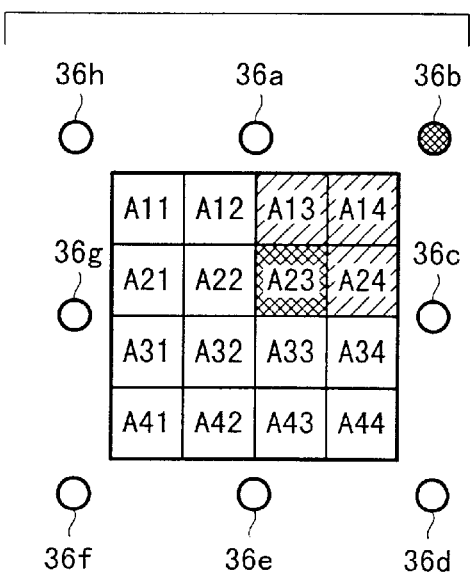
FIG. 10C is a view showing a display pattern on the display unit when display elements in the direction of 01:30 are turned on in the pseudo 4×4 pixel detecting process that is carried out when the radiation source is positioned within the area sensor.
Figure 10D:
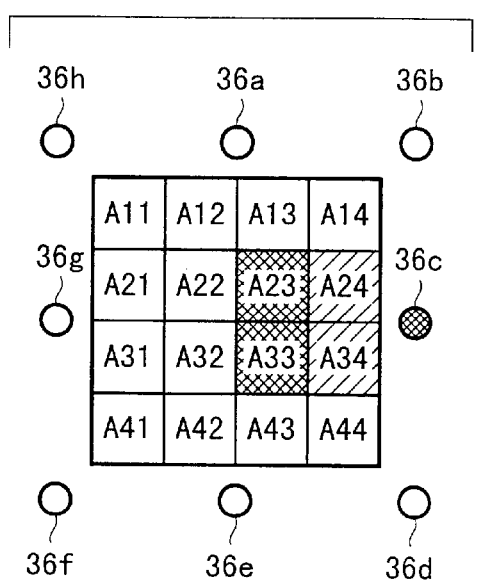
FIG. 10D is a view showing a display pattern on the display unit when display elements in the direction of 03:00 are turned on in the pseudo 4×4 pixel detecting process that is carried out when the radiation source is positioned within the area sensor.

Specifically, in FIG. 10A, maximum counts C are present in the pixels A22, A23, and smaller counts C are present in the pixels A12, A13. In this case, the display element 36a in the direction of 12:0 is turned on in the high-luminance level. In FIG. 10B, a maximum count C is present in the pixel A22, and smaller counts C are present in the pixels A11, A12, A21. In this case, the display element 36h in the direction of 10:30 is turned on in the high-luminance level. In FIG. 10C, a maximum count C is present in the pixel A23, and smaller counts C are present in the pixels A13, A14, A24. In this case, the display element 36b in the direction of 01:30 is turned on in the high-luminance level. In FIG. 10D, maximum counts C are present in the pixels A23, A33, and smaller counts C are present in the pixels A24, A34. In this case, the display element 36c in the direction of 03:00 is turned on in the high-luminance level.

Prior to the calculation of the direction and distance in step S17, if the radiation source 200 is small in size, then the number of pixels on one side of the pseudo pixel assembly may be set to a larger value, e.g., $n=2^P$ (p=3 or 4) for displaying a greater number of pixels to specify the position of the radiation source 200 more accurately.

In the above embodiment, as described above, when the examinee dosed with a radioisotope is scanned by the area sensor 32, the display elements 36a through 36h of the position/direction display units 34A, 34B display a pattern indicative of the position/direction of the radiation source the examinee. By operating the gamma camera 12 according to the displayed pattern, the operator of the gamma camera 12 can detect the position of the radiation source, i.e., the accumulated position of the radioisotope, reliably within a short period of time.

The position/direction of the radiation source in the examinee is also indicated by sound or voice sound to the operator of the gamma camera 12, the operator can recognize the radiation source through the auditory sense. The sound an intensity that becomes progressively greater as the gamma camera 12 is closer to the radiation source, and/or at progressively varying frequencies, i.e., at a pitch that becomes progressively higher as the gamma camera 12 is closer to the radiation source. The voice sound may represent the direction of the radiation source as the direction of a time on an analog clock.

In order to determine the position/direction of a radiation source, the area sensor 32 may be arranged to for identifying either a back-and-forth direction or a lateral direction, or may be arranged to comprise at least four (2×2) detecting elements (detecting pixels) for identifying both a back-and-forth direction and a lateral direction. The number of detecting elements is not limited to a power of 2 such as 2×2, but may be 2×3, 4×5, or the like. Generally, if the number of detecting elements is represented by n×m, each of n and m should preferably be 2 or greater. The number and shape of detecting elements may be selected depending on the shape of a radiation source in the examinee.

In the present embodiment, since a radiation source distribution determined by the signal processor 38 is displayed on the display unit 122, the operator can recognize the radiation source distribution in the examinee at a glance. The pixel arrangement of the display unit 122 may be changed to a 1 pixel, 2×2 pixels, 4×4 pixels, 8×8 pixels, or 16×16 pixels for indicating the radiation source distribution in the examinee.

Another operation sequence of the radiation source detecting system 10 shown in FIG. 1, which uses the display unit 122 as an image display unit and/or a position/direction display unit, will be described below with reference to FIG. 11.

Figure 11:
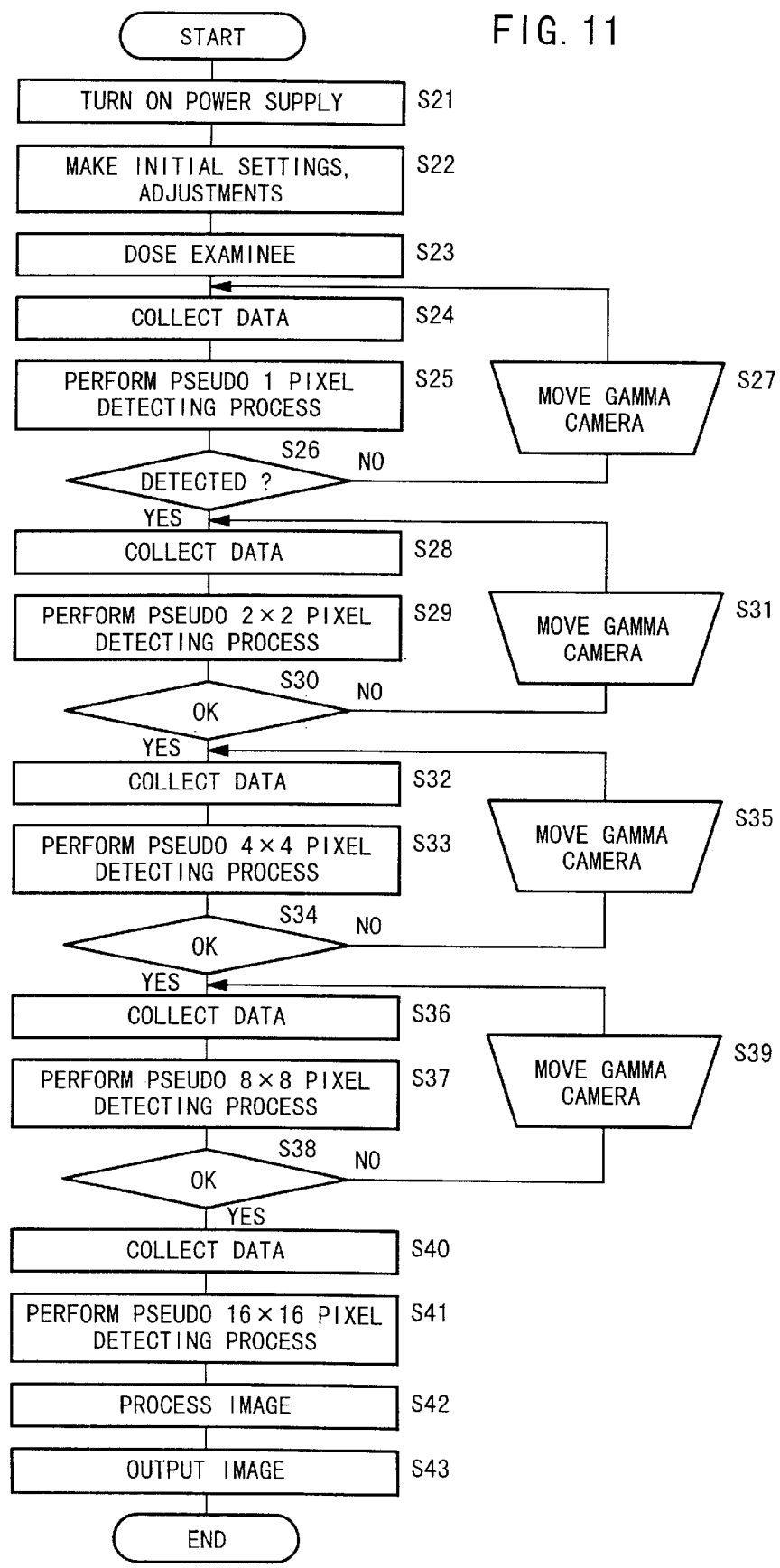
FIG. 11 is a flowchart of another operation sequence of the radiation source detecting system shown in FIG. 1.

In FIG. 11, the processing in steps S21 through S24 is the same as the processing in steps S1 through S4, and will not be described below for the sake of brevity.

In step S25, the pseudo 1 pixel detecting process is carried out.

Figure 12:
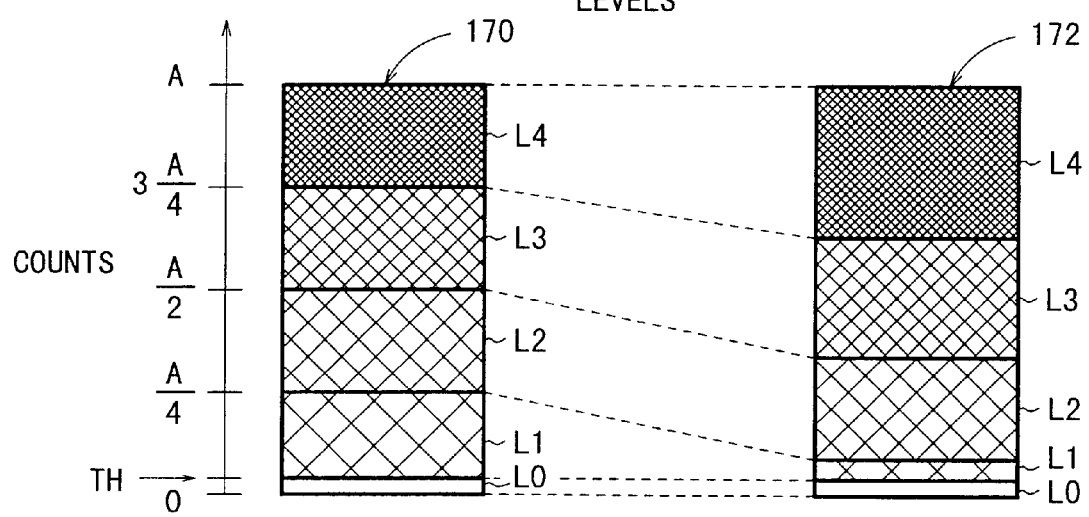
FIG. 12 is a diagram showing the relationship of displayed luminance levels or headphone sound levels to counts of gamma rays used in a pseudo 1 pixel detecting process.

A maximum count outputted from one semiconductor detecting element 50 is represented by $(2_N-1)$, and a sum count C produced by adding the output signals from the 256 semiconductor detecting elements 50 in the pseudo 1 pixel detecting process is represented by $(2^N-1) \times 256$ (=A). For locating an afflicted local region in the examinee in a short period of time, an association table 170 shown in FIG. 12 is employed which has some display image luminance levels corresponding to sum counts. The association table 170 includes a minimum image luminance level (first luminance level) L0 that is used when the sum count C ranges from 0 to the threshold TH inclusive, a next minimum image luminance level (second luminance level) L1 that is used when the sum count C ranges from the threshold TH to a value A/4, an image luminance level (third luminance level) L2 that is used when the sum count C ranges from the value A/4 to a value A/2, an image luminance level (fourth luminance level) L3 that is used when the sum count C ranges from the value A/2 to a value 3A/4, and a highest luminance level (fifth luminance level) L4 that is used when the sum count C ranges from the value 3A/4 to a value A inclusive.

FIG. 12 shows another association table 172 in which the relationship between the counts and the luminance levels is more nonlinear than the association table 170. The association tables 170, 172 are also used to determine the levels of audio outputs. For example, no sound is outputted at the first luminance level L0, and sound is outputted at a maximum level at the fifth luminance level L4. The sound level may be an amplitude level or a frequency level. In this manner, the sound can be outputted in divided gradation levels. In the present embodiment, the association table 170 is employed.

Figure 13A:
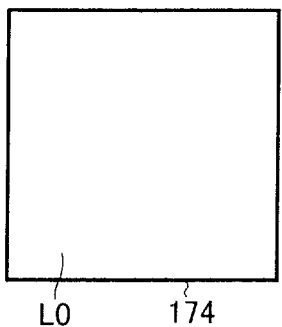
FIG. 13A is a view showing a uniform image at a minimum luminance level displayed according to the pseudo 1 pixel detecting process.

If the sum count C ranges from the value 0 to the threshold TH in the 1 pixel detecting process in step S25, then the display unit 122 displays a uniform image 174 at the minimum luminance level (first luminance level) L0, as shown in FIG. 13A. The image 174 has a size of 16 pixels×16 pixels=256 pixels. However, the image 174 may be scaled up or down into an image of original size.

If no radiation source is detected in step S26 while the uniform image 174 at the minimum luminance level (first luminance level) L0 is being displayed, then the operator moves the gamma camera 12 to another location on the examinee in step S27, after which the data collection process and the 1 pixel detecting process are carried out again in steps S24, S25.

Figure 13B:
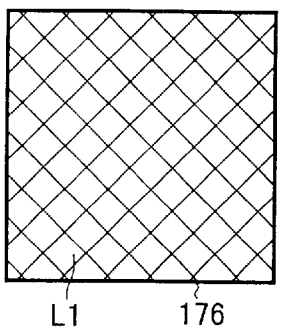
FIG. 13B is a view showing a uniform image at a next minimum luminance level displayed according to the pseudo 1 pixel detecting process.

If the sum count C in the 1 pixel detecting process is greater than the threshold TH, indicating the detection of a radiation source, in step S26, then the display unit 122 displays a uniform image 176 at the second luminance level L1, as shown in FIG. 13B. At the same time, the operator can hear a sound corresponding to the second luminance level L1 from the headphones 65. The operator can perceive the sound in the center of the head.

At this time, the operator knows that the radiation source in the examinee is close to the gamma camera 12. The operator may change the displayed 1-pixel image to a 16×16 pixel image.

In step S28, the microcomputer 160 collects radiation data again. In step S29, the 1 pixel detecting process changes to the 2×2 pixel detecting process either manually or automatically.

In the 2×2 pixel detecting process, as described above with reference to FIG. 7, the sum of counts C from the 16-channel counters 158a through 158d associated respectively with the detectors 150a through 150d is regarded as representing one pixel, the sum of counts C from the 16-channel counters 158e through 158h associated respectively with the detectors 150e through 150h is regarded as representing one pixel, the sum of counts C from the 16-channel counters 158i through 158l associated respectively with the detectors 150i through 150l is regarded as representing one pixel, and the sum of counts C from the 16-channel counters 158m through 158p associated respectively with the detectors 150m through 150p is regarded as representing one pixel, so that the gamma camera 12 will operate as having a total of 2×2 pixels. In the 1 pixel detecting process, the gamma camera 12 operates as having a single pixel.

Figure 14:
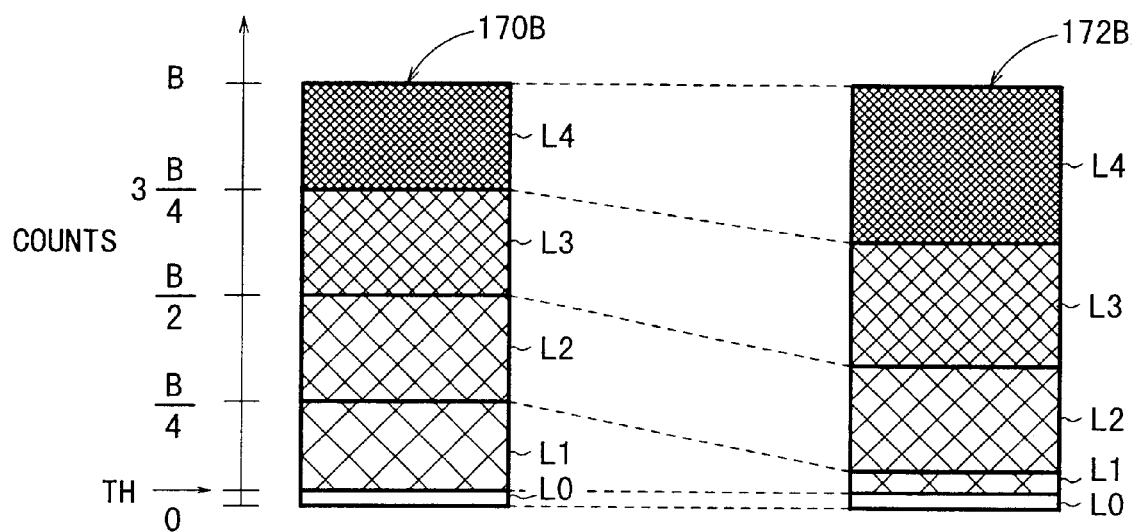
FIG. 14 is a diagram showing the relationship of image display luminance levels or headphone sound levels to counts of a radiation used in the pseudo 2×2 pixel detecting process.

The sum count C produced by adding the output signals from the 64 semiconductor detecting elements 50 is represented by $(2^N-1)\times 64$ (=B). As shown in FIG. 14, an association table 170B shows the relationship between image display luminance levels or headphone sound levels and counts in the 2×2 pixel detecting process. The association table 170B includes a fifth luminance level L4 which exceeds a count 3B/4 up to a count B. An association table 172B which is more nonlinear than the association table 170B may also be employed.

Figure 13C:
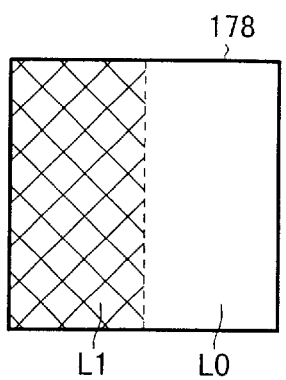
FIG. 13C is a view showing a luminance-modulated image displayed according to a pseudo 2×2 pixel detecting process.
Figure 13D:
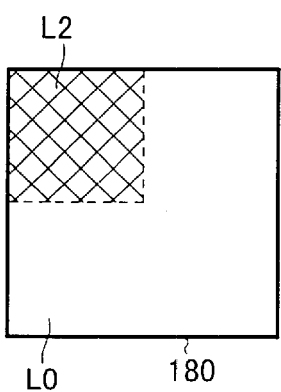
FIG. 13D is a view showing another luminance-modulated image displayed according to the pseudo 2×2 pixel detecting process.

In the 2×2 pixel detecting process, the display unit 122 displays an image 178 divided into four parts as shown in FIG. 13C or an image 180 divided into four parts as shown in FIG. 13D.

By looking at the image 178 in the 2×2 pixel detecting process or hearing sound from only the left ear via one of the headphones 65, the operator of the gamma camera 12 can move the gamma camera 12 to the left more closely to the radiation source.

Until a desired image is displayed, or until a decision of OK is reached in step S30, the operator can move the gamma camera 12 in step S31.

Figure 13E:
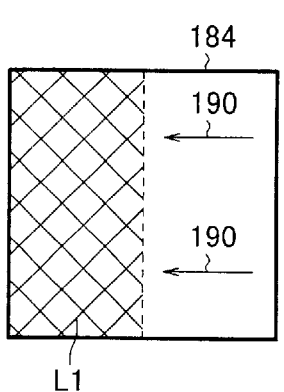
FIG. 13E is a view showing still another luminance-modulated image displayed according to the pseudo 2×2 pixel detecting process.
Figure 13F:
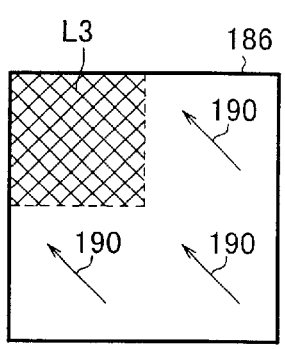
FIG. 13F is a view showing an arrow display image displayed according to the pseudo 2×2 pixel detecting process.

In the 2×2 pixel detecting process, the display unit 122 may display an image 184 as shown in FIG. 13E which corresponds to the image 178 as shown in FIG. 13C or an image 186 as shown in FIG. 13F which corresponds to the image 180 divided as shown in FIG. 13D.

In the images 184, 186, only the pixels at the maximum luminance level are displayed by way of luminance modulation, and other pixels are displayed as arrows 190 pointing toward the pixels at the maximum luminance level.

By looking at the images 184, 186, the operator can easily move the gamma camera 12 in the direction indicated by the arrows 190 to reach the radiation source, i.e., the afflicted local region, in the examinee.

Figure 13G:
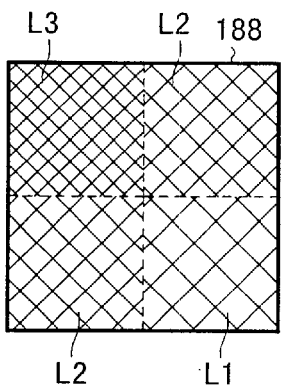
FIG. 13G is a view showing another arrow display image displayed according to the pseudo 2×2 pixel detecting process.

By thus moving the gamma camera 12, the display unit 122 now displays an image 188 as shown in FIG. 13G, for example.

Figure 13H:
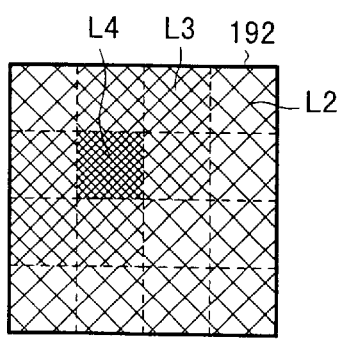
FIG. 13H is a view showing a luminance-modulated image displayed according to a pseudo 4×4 pixel detecting process.
Figure 13I:
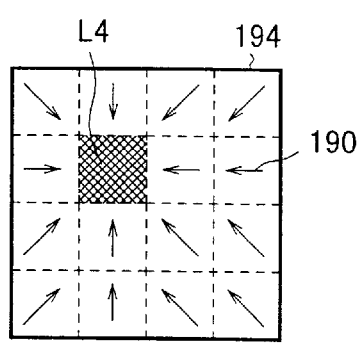
FIG. 13I is a view showing an arrow display image displayed according to the pseudo 4×4 pixel detecting process.

Then, the operator can display a luminance-modulated image 192 as shown in FIG. 13H or an allow display image 194 as shown in FIG. 13I, which corresponds to the luminance modulated image 192, in a 4×4 pixel detecting process in steps S32 through S35.

Thereafter, an 8×8 pixel detecting process in steps S36 through S39 is carried out. When a radiation source, e.g., a most intensive center of a radiation source, is captured in the displayed image on the display unit 122, a 16×16 pixel detecting process in steps S40, S41, i.e., a detecting process in a fully displayed image, is carried out.

The fully displayed image is stored in the hard disk 133 of the personal computer 22.

Figure 15:
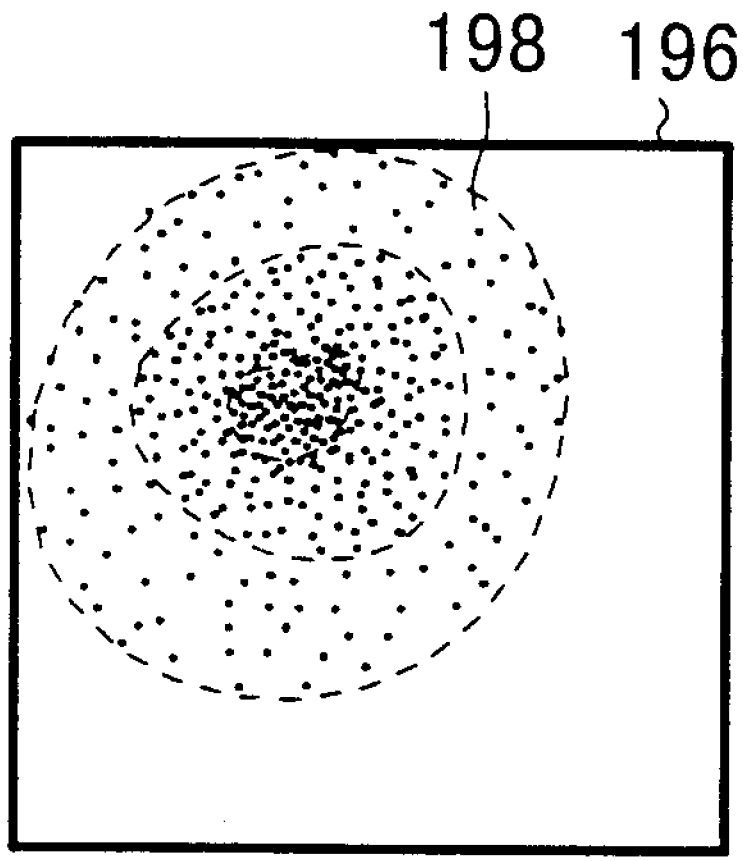
FIG. 15 is a view showing an example of an image representing a detected radiation source.

The image capturing process is now put to an end. In step S42, the image is processed for smoothing, edge emphasis, size enlargement, etc. according to known image processing sequences. Then, the processed image is outputted in step S43 to enable the display unit 122 to display an image 196 including a radiation image 198 of an afflicted local region in the examinee as shown in FIG. 15.

The image 196 including the radiation image 198 may also be printed as a hard copy by the printer 26.

The hard copy gives clinically useful information to the operator, who may be a medical doctor. Therefore, the radiation source detecting system 10 allows the operator to obtain clinically useful information quickly and accurately.

In the present embodiment, the pulse signals outputted from the 16 detectors 150a through 150p of the gamma camera 12 (area sensor 32) that can manually be operated to scan the examinee are counted by the 16-channel counters 158a through 158p, and the counts C from the 16-channel counters 158a through 158p are stored. The microcomputer 160 of the signal processor 38 processes the stored counts into an image signal for displaying a pattern indicative of the position/direction of the radiation source in the examinee on the display unit 122 of the personal computer 22.

Then, the operator moves the gamma camera 12 to and in the position/direction indicated by the displayed pattern, thus detecting the position of the radiation source, i.e., the accumulated position of the radioisotope, reliably within a short period of time.

The pattern indicative of the position/direction of the radiation source may be represented by a luminance difference corresponding to the magnitude of signals outputted from the detectors 150, allowing the operator to visually recognize easily the direction in which to move the gamma camera 12.

The microcomputer 160 also converts the counts C to an audio signal, or more specifically an audio signal which is represented by the intensity (amplitude) or frequency of the sound corresponding to the counts C and which can be heard in back-and-forth and lateral directions in the head of the operator, and the audio signal is outputted from the headphones 65. Thus, the operator can move the gamma camera 12 in the direction of the recognized sound, thus determining the direction of the radiation source easily via the auditory sense.

By combining a certain number of counts C, the pulse signals outputted from a corresponding number of semiconductor detecting devices 50 are substantially combined with each other. While one semiconductor detecting device 50 has a detecting area of 2 mm×2 mm, a radiation source can initially be detected with the total area of 32 mm×32 mm of the entire area sensor 32. In this manner, the period of time required to locate a radiation source initially can be shortened.

In the present embodiment, the radiation source detecting system 10 has the area sensor 32 comprising 256 semiconductor detecting devices 50 and as many memories (the 16-channel counters 158 or the RAM 166 (see FIG. 14)) as the number of the semiconductor detecting devices 50 for storing the output signals from the semiconductor detecting devices 50. The CPU 162 reads the counts C as the output signals from the semiconductor detecting devices 50 from the memories, combines a certain number of counts C or all the counts C, and displays an image or outputs an audio signal based on the sum count or counts. Therefore, even if a radiation source is detected in a small range corresponding to several of the semiconductor detecting devices 50, it can be confirmed by a displayed image in a wide range as shown in FIGS. 13B, 13C or by an audio output signal, the operator can easily detect the radiation source.

In the present embodiment, when the position of a radiation source is to be detected by the area sensor 32 which has a radiation detecting area (32 mm×32 mm) X provided by a plurality of semiconductor detecting devices 50, the output signals from all the semiconductor detecting devices 50 are combined to cause the area sensor 32 to function as one radiation detecting element without changing the radiation detecting area X, for detecting a radiation source. This process is referred to as a first step which corresponds to the processing in step S25.

Then, the output signals from a certain number of semiconductor detecting devices 50 are combined to cause the area sensor 32 to function as a reduced number of radiation detecting elements without changing the radiation detecting area X, for detecting a radiation source. This process is referred to as a second step which corresponds to the processing in step S29, for example.

Then, without changing the radiation detecting area X, a greater number of semiconductor detecting devices 50 are combined to cause the area sensor 32 to function as a greater number of radiation detecting elements for detecting a radiation source. This process is referred to as a third step which corresponds to the processing in step S33 or S37, for example. The third step may include the second step.

Finally, all the semiconductor detecting devices 50 are individually used for detecting a radiation source. This process is referred to as a fourth step which corresponds to the processing in step 40.

The above detecting process allows a radiation source to be detected in a wide area. When a radiation source is detected or sometime within the detecting process, a detailed image can be displayed based on the output signal from the area sensor 32.

The first step for combining all the semiconductor detecting devices 50 into one pixel may be dispensed with.

Figure 16:
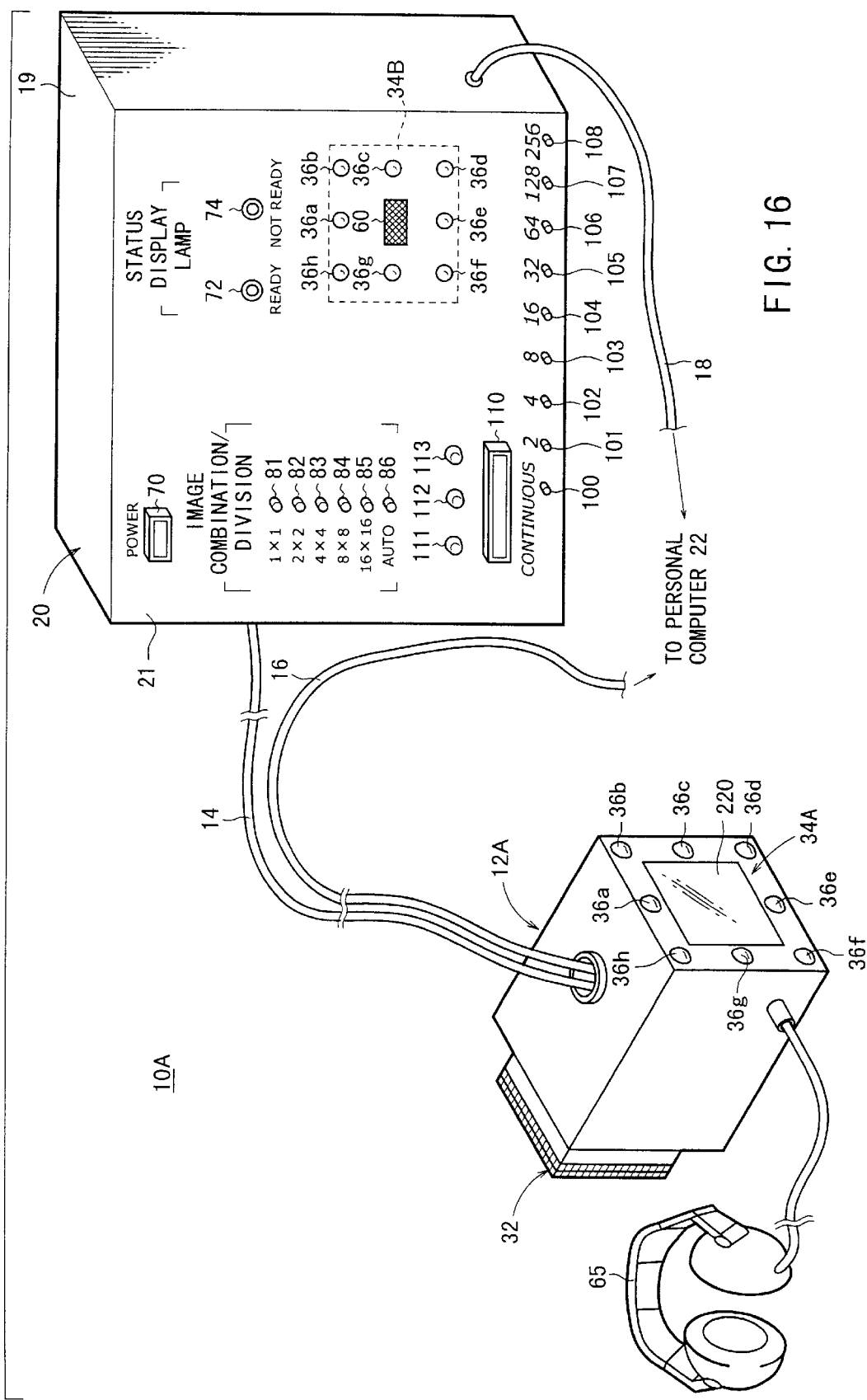
FIG. 16 is a perspective view of a radiation source detecting system according to another embodiment of the present invention.

FIG. 16 shows a radiation source detecting system 10A according to another embodiment of the present invention. Those parts of the radiation source detecting system 10A which correspond or are identical to the radiation source detecting system 10 shown in FIGS. 1 and 2 are denoted by corresponding or identical reference characters, and will not be described in detail below.

The radiation source detecting system 10A shown in FIG. 16 has a gamma camera 12A with a display unit 220, such as a liquid crystal display unit or the like, disposed centrally on its rear panel. The display unit 220 displays a distribution and/or a position/direction of a radiation source. Thus, the gamma camera 12A alone allows the operator to know the distribution and/or the position/direction of the radiation source.

Figure 17:
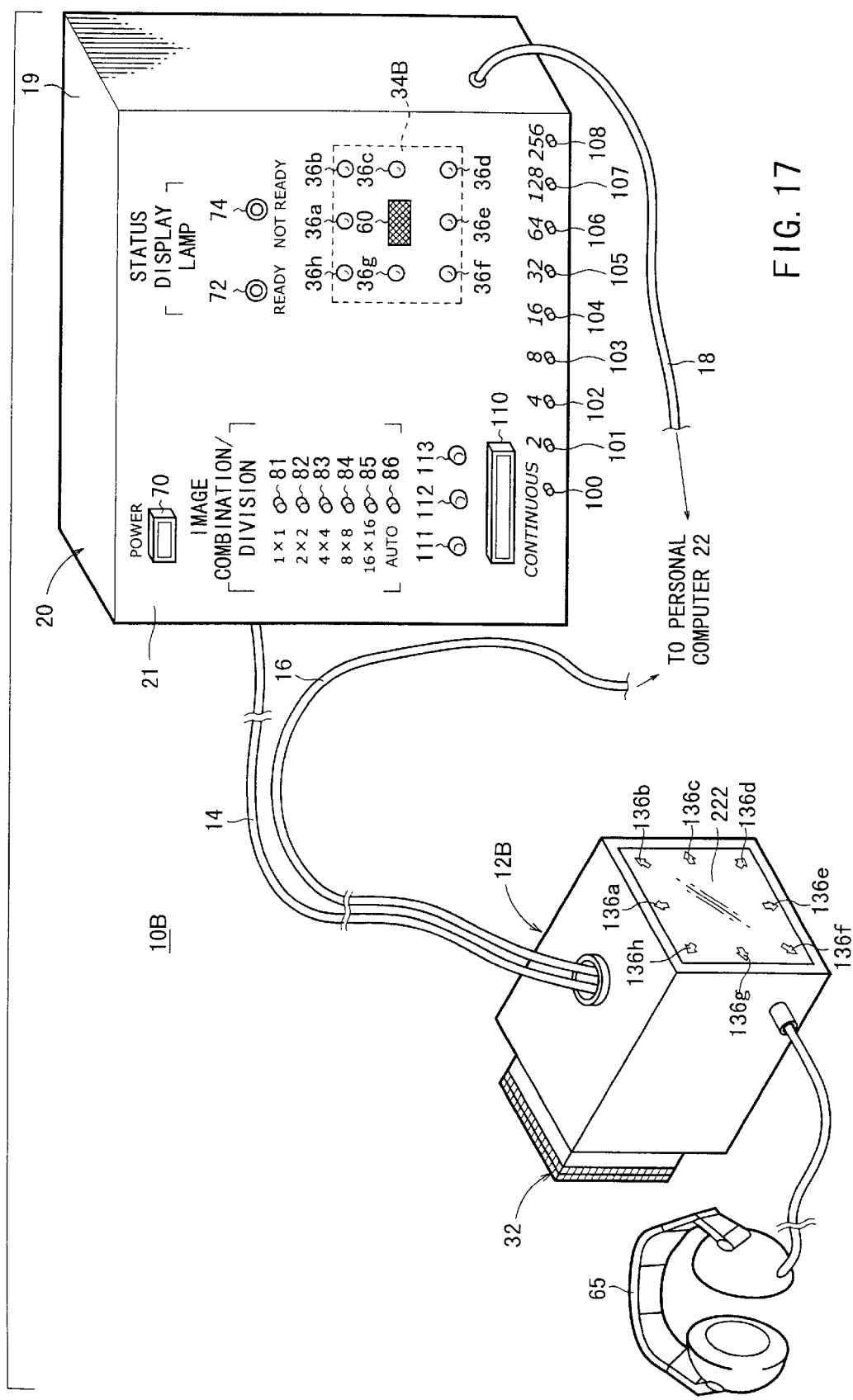
FIG. 17 is a perspective view of a radiation source detecting system according to still another embodiment of the present invention.

FIG. 17 shows a radiation source detecting system 10B according to still another embodiment of the present invention. Those parts of the radiation source detecting system 10B which correspond or are identical to the radiation source detecting system 10 shown in FIGS. 1 and 2 are denoted by corresponding or identical reference characters, and will not be described in detail below.

The radiation source detecting system 10B shown in FIG. 17 has a gamma camera 12B with a display unit 222, such as a liquid crystal display unit or the like, disposed centrally on its rear panel. The display unit 222 displays arrow indicators (arrow indicating regions) 136a through 136h as an image for indicating the position/direction of a radiation source. The arrow indicators 136a through 136h are used as a substitute for the display elements 36a through 36h in the form of LEDs.

When a certain one of the arrow indicators 136a through 136h in the image displayed on the display unit 222 is turned on or flickered, the operator can confirm the position/direction of a radiation source. At the same time, the operator can confirm an intensity distribution of the radiation source as a 16×16 pixel image, for example, in a region of the display unit 222 surrounded by the arrow indicators 136a through 136h.

In the embodiment shown in FIG. 17, the position/direction display unit 34A comprising LEDs on the gamma cameras 12, 12A shown in FIGS. 2 and 16 are not required. Therefore, the display unit 222 doubles as a position/direction display unit and an image display unit.

Figure 18:
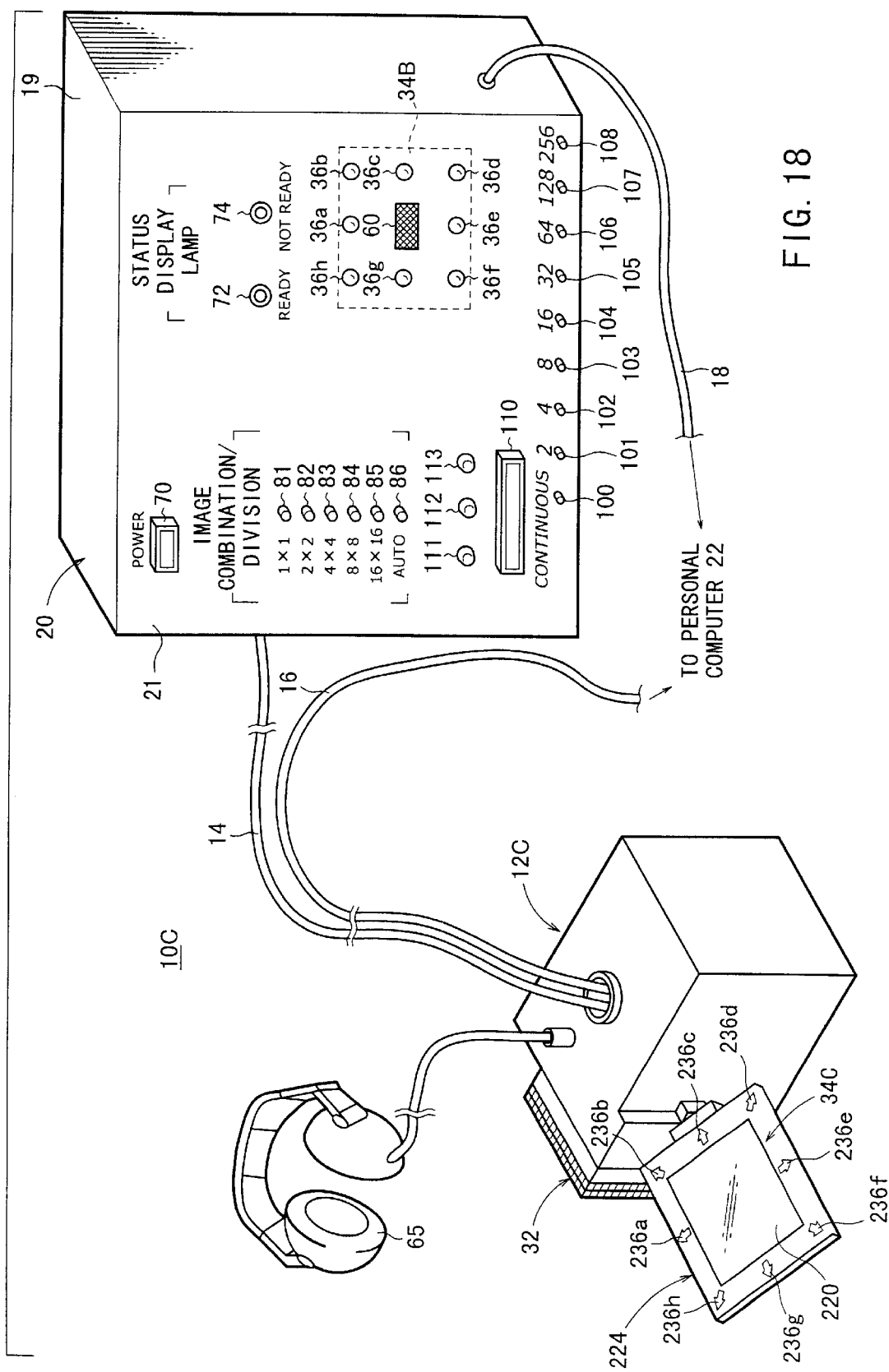
FIG. 18 is a perspective view of a radiation source detecting system according to yet another embodiment of the present invention.

FIG. 18 shows a radiation source detecting system 10C according to yet another embodiment of the present invention. Those parts of the radiation source detecting system 10C which correspond or are identical to the radiation source detecting system 10 shown in FIGS. 1 and 2 are denoted by corresponding or identical reference characters, and will not be described in detail below.

The radiation source detecting system 10C shown in FIG. 18 has a gamma camera 1C having a display device 224 which comprises a liquid crystal display unit on a side panel thereof. The display device 224 can be turned 90° toward the area sensor 32 or toward the rear panel of the gamma camera 1C.

The display device 224 has a position/direction indicator unit 34C disposed around the display unit 220 thereof and comprising arrow indicators (arrow indicating regions) 236a through 236h in the form of LEDs for indicating the position/direction of a radiation source.

The operator can confirm an intensity distribution of a radiation source on the display unit 220, and at the same time confirm the position/direction of the radiation source when a certain one of the arrow indicators 236a through 236h around the display unit 220 is turned on or flickered.

The gamma camera 12C shown in FIG. 18 may have a liquid crystal display device on its rear panel or have a loudspeaker 60 mounted in a suitable position thereon.

The principles of the present invention are also applicable to a gamma camera having an area sensor which comprises a plurality of scintillator elements and a positive-sensitive photomultiplier in combination.

According to the present invention, as described above, since a distribution of a radiation source detected by an area sensor comprising a plurality of detecting elements is displayed on the image display unit, the distribution of the radiation source can be displayed with a simple arrangement.

Furthermore, because the position/direction of the radiation source is displayed on the position/direction display unit, the operator of the area sensor can detect the radiation source easily within a short period of time. Thus, the position of the radiation source can be detected in a short period of time and reliably.

With the area sensor (essentially the gamma camera) employing a plurality of semiconductor detecting elements, the radiation source detecting system may be small in size, manually operable, and handled with ease.

Although certain preferred embodiments of the present invention have been shown and described in detail, it should be understood that various changes and modifications may be made therein without departing from the scope of the appended claims.

What is claimed is:

1. An apparatus for detecting a radiation source, comprising:
   an area sensor having a plurality of detecting elements for detecting a radiation emitted from a radiation source in an examinee;
   a signal processor for determining a position of the radiation source relative to the position of said area sensor on said examinee based on signals outputted from said detecting elements and for determining a direction for moving said area sensor on said examinee to approach said radiation source; and
   a position/direction display unit for displaying the determined position of the radiation source relative to the position of said area sensor on said examinee, and for indicating said direction for moving said area sensor on said examinee to approach said radiation source.

2. An apparatus according to claim 1, wherein said position/direction display unit comprises a plurality of display areas for displaying the determined position of the radiation source and said direction for moving said area sensor.

3. An apparatus according to claim 2, wherein said display areas comprise arrow indicators disposed in a radial pattern.

4. An apparatus according to claim 2, wherein said signal processor comprises means for controlling flickering intervals of said display areas depending on the determined position of the radiation source and said direction for moving said area sensor.

5. An apparatus according to claim 2, wherein said signal processor comprises means for controlling displayed luminance levels of said display areas depending on the determined position of the radiation source and said direction for moving said area sensor.

6. An apparatus according to claim 1, wherein each of said detecting elements comprises a CdTe or a CdZnTe semiconductor detecting element.

7. An apparatus according to claim 1, wherein said detecting elements comprise n×m (n, m represent at least 2) detecting elements.

8. An apparatus for detecting a radiation source, comprising:
   an area sensor having a plurality of detecting elements for detecting a radiation emitted from a radiation source in an examinee;
   a signal processor for determining a distribution and a position of the radiation source relative to the position of said area sensor on said examinee based on signals outputted from said detecting elements and for determining a direction for moving said area sensor on said examinee to approach said radiation source; and
   a display unit for displaying the determined distribution and position of the radiation source relative to the position of said area sensor on said examinee, and for indicating said direction for moving said area sensor on said examinee to approach said radiation source.

9. An apparatus according to claim 8, wherein said display unit comprises a single display unit including a display area for displaying the distribution of the radiation source and a display area for displaying the position of the radiation source and said direction for moving said area sensor.

10. An apparatus according to claim 8, wherein said display unit comprises a display area for displaying the distribution of the radiation source and a display area separate from said display area, for displaying the position of the radiation source and said direction for moving said area sensor.

11. An apparatus for detecting a radiation source, comprising:
    a main unit having a prismatic shape;
    an area sensor disposed in a portion of said main unit and having a plurality of detecting elements for detecting a radiation emitted from a radiation source in an examinee;
    a signal processor for determining a distribution and a position of the radiation source relative to the position of said area sensor on said examinee based on signals outputted from said detecting elements and for determining a direction for moving said area sensor on said examinee to approach said radiation source; and
    a display unit disposed in another portion of said main unit, for displaying the determined distribution and position of the radiation source relative to the position of said area sensor on said examinee, and for indicating said direction for moving said area sensor on said examinee to approach said radiation source.

12. An apparatus for detecting a radiation source, comprising:
    an area sensor having a plurality of detecting elements for detecting a radiation emitted from a radiation source in an examinee;
    a signal processor for processing signals outputted from said detecting elements into an audio signal, said signal processor determining a position of the radiation source relative to the position of said area sensor on said examinee based on signals outputted from said detecting elements and for determining a direction for moving said area sensor on said examinee to approach said radiation source; and
    audio output means for outputting sound and/or voice sound based on the audio signal from said signal processor;
    said signal processor comprising means for controlling said audio output means to generate sound and/or voice sound indicative of a position of said radiation source relative to a position of said area sensor on said examinee, and for indicating said direction for moving said area sensor on said examinee to approach said radiation source.

13. An apparatus according to claim 12, wherein said sound indicative of the position of said radiation source and said direction for moving said area sensor comprises a sound having a predetermined intensity and/or a predetermined frequency.

14. An apparatus according to claim 12, wherein said voice sound indicative of the position of said radiation source and said direction for moving said area sensor comprises a voice sound representing the direction of a time on an analog clock whose center is regarded as the center of said area sensor.

15. A method of detecting the position of a radiation source with an area sensor having a plurality of radiation detecting elements which provide a radiation detecting surface, comprising subsequent steps of:
    initially, combining a predetermined number of output signals from said radiation detecting elements to cause said area sensor to function as a reduced number of radiation detecting elements without changing the area of said radiation detecting surface;

thereafter, combining a progressively reduced number of output signals from said radiation detecting elements to cause said area sensor to function as a progressively increased number of radiation detecting elements without changing the area of said radiation detecting surface; and finally, causing said area sensor to function as said plurality of radiation detecting elements.

16. A method of detecting the position of a radiation source with an area sensor having a plurality of radiation detecting elements which provide a radiation detecting surface, comprising subsequent steps of:

initially, combining all output signals from said radiation detecting elements to cause said area sensor to function as a single radiation detecting element without changing the area of said radiation detecting surface;

thereafter, combining a predetermined number of output signals from said radiation detecting elements to cause said area sensor to function as a reduced number of radiation detecting elements without changing the area of said radiation detecting surface;

thereafter, combining a progressively reduced number of output signals from said radiation detecting elements to cause said area sensor to function as a progressively increased number of radiation detecting elements without changing the area of said radiation detecting surface; and finally, causing said area sensor to function as said plurality of radiation detecting elements.

* * * * *